United States Patent
Matteucci et al.

(10) Patent No.: US 10,668,047 B2
(45) Date of Patent: Jun. 2, 2020

(54) AZIRIDINE CONTAINING DNA ALKYLATING AGENTS

(71) Applicant: Molecular Templates Inc., Austin, TX (US)

(72) Inventors: Mark Matteucci, Austin, TX (US); Xiaohong Cai, Austin, TX (US); Yeyu Cao, Austin, TX (US); Hailong Jiao, Austin, TX (US); Jing Yuan Ma, Austin, TX (US); Jian-Xin Duan, Austin, TX (US)

(73) Assignee: Molecular Templates, Inc., Austin, TX (US)

( * ) Notice: Subject to any disclaimer, the term of this patent is extended or adjusted under 35 U.S.C. 154(b) by 0 days.

(21) Appl. No.: 16/392,477

(22) Filed: Apr. 23, 2019

(65) Prior Publication Data

US 2020/0085786 A1 Mar. 19, 2020

Related U.S. Application Data

(63) Continuation of application No. 15/736,285, filed as application No. PCT/US2016/039092 on Jun. 23, 2016, now abandoned.

(Continued)

(51) Int. Cl.
*A61K 31/396* (2006.01)
*A61K 31/4168* (2006.01)
(Continued)

(52) U.S. Cl.
CPC ........ *A61K 31/396* (2013.01); *A61K 31/4168* (2013.01); *A61K 31/4178* (2013.01);
(Continued)

(58) Field of Classification Search
CPC .............. A61K 31/396; A61K 31/4168; A61K 31/4178; A61K 31/675
(Continued)

(56) References Cited

U.S. PATENT DOCUMENTS 5,472,956 A 12/1995 Borch et al.
6,482,953 B1 11/2002 Kim et al.
(Continued)

FOREIGN PATENT DOCUMENTS

CN 102924507 A 2/2013
JP 2018-513876 A 5/2018
(Continued)

OTHER PUBLICATIONS

Chen, Y. et al., "Design of anticancer prodrugs for reductive activation", Medicinal Research Reviews, vol. 29, No. 1, 2009, pp. 29-64.

(Continued)

*Primary Examiner* — Niloofar Rahmani
(74) *Attorney, Agent, or Firm* — Foley & Lardner LLP

(57) ABSTRACT

Provided herein are compounds of formula (I)-(VI):

(Continued)

-continued

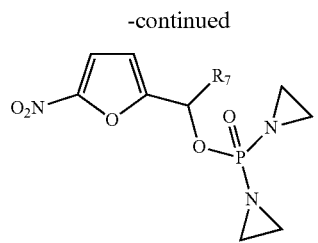

(VI)

wherein the variables are defined herein, processes of making them, and methods of treating cancer comprising administering such compounds.

11 Claims, 3 Drawing Sheets

Related U.S. Application Data

(60) Provisional application No. 62/184,129, filed on Jun. 24, 2015.

(51) Int. Cl.
| | |
|---|---|
| *A61K 31/4178* | (2006.01) |
| *C07F 9/6558* | (2006.01) |
| *C07F 9/6561* | (2006.01) |
| *A61K 31/675* | (2006.01) |
| *A61P 35/00* | (2006.01) |
| *A61K 31/665* | (2006.01) |
| *C07F 9/564* | (2006.01) |

(52) U.S. Cl.
CPC .......... *A61K 31/665* (2013.01); *A61K 31/675* (2013.01); *A61P 35/00* (2018.01); *C07F 9/564* (2013.01); *C07F 9/6561* (2013.01); *C07F 9/65583* (2013.01); *C07F 9/65586* (2013.01)

(58) Field of Classification Search
USPC .................. 514/83, 94, 132, 99; 549/6, 218; 548/119
See application file for complete search history.

(56) References Cited

U.S. PATENT DOCUMENTS

| | | | |
|---|---|---|---|
| 8,507,464 | B2 | 8/2013 | Matteucci et al. |
| 2004/0214798 | A1 | 10/2004 | Hu |
| 2008/0269268 | A1 | 10/2008 | Schirok et al. |
| 2010/0256139 | A1 | 10/2010 | Rockway et al. |
| 2011/0251159 | A1 | 10/2011 | Matteucci et al. |
| 2014/0010805 | A1 | 1/2014 | Hart et al. |
| 2014/0170240 | A1 | 6/2014 | Matteucci et al. |
| 2018/0044360 | A1* | 2/2018 | Duan .................... C07F 9/2466 |

FOREIGN PATENT DOCUMENTS

| | | |
|---|---|---|
| WO | WO-2004/087075 | 10/2004 |
| WO | WO-2006/057946 A2 | 6/2006 |
| WO | WO-2007/002931 A2 | 1/2007 |
| WO | WO-2007/098089 A2 | 8/2007 |
| WO | WO-2008/083101 A1 | 7/2008 |
| WO | WO-2008/151253 A1 | 12/2008 |
| WO | WO-2009/018163 A1 | 2/2009 |
| WO | WO-2010/044686 A1 | 4/2010 |
| WO | WO-2010/048330 A1 | 4/2010 |
| WO | WO-2011/066416 A1 | 6/2011 |
| WO | WO-2014/131023 A1 | 8/2014 |
| WO | WO-2015/051921 A1 | 4/2015 |
| WO | WO-2016/145092 A1 | 9/2016 |
| WO | WO-2016/161342 A2 | 10/2016 |
| WO | WO-2016/210175 A1 | 12/2016 |
| WO | WO-2017/087428 A1 | 5/2017 |

OTHER PUBLICATIONS

Communication pursuant to Rules 70(2) and 70a(2) EPC issued in EP 16815334.4 dated Jan. 8, 2019, 1 page.
Duan, J-X. et al. (2008) "Potent and Highly Selective Hypoxia-Activated Achiral Phosphoramidate Mustards as Anticancer Drugs," J. Med Chem 51:2412-2420.
Extended European search report issued in 16762438.6 dated Jul. 3, 2018, 10 pages.
Extended European Search Report issued in 16774352.5 dated Nov. 6, 2018, 11 pages.
Extended European Search Report issued in 16815334.4 dated Dec. 21, 2018, 7 pages.
Final Office Action on U.S. Appl. No. 15/563,481 dated Apr. 22, 2019.
Golub, T.R. et al. (1999) "Molecular Classification of Cancer: Class Discovery and Class Prediction by Gene Expression Monitoring," Science 286:531-537.
Guise, C.P. et al. (2014) "Bioreductive prodrugs as cancer therapeutics: targeting tumor hypoxia," Chinese Journal of Cancer 33(2):80-86.
Hay et al. Substituent effects on the kinetics of reductively-initiated fragmentation of nitrobenzyl carbamates designed as triggers for bioreductive prodrugs, J. Chem. Soc., Perkin Trans. 1, 1999, 2759-2770. (Year:1999).
Hu et al., "Synthesis and structure-activity relationships of nitrobenzyl phosphoramide mustards as nitroreductase-activated prodrugs", Bioorganic & Medicinal Chemistry Letters 21 (2011) 3986-3991.
International Application No. PCT/US2015/040642, International Preliminary Report on Patentability dated Jan. 26, 2017, 7 pages.
International Application No. PCT/US2015/040642, International Search Report and Written Opinion dated Sep. 29, 2015, 9 pages.
International Preliminary Report on Patentability issued in PCT/US2016/039092 dated Jan. 4, 2018, 9 pages.
International Search Report and Written Opinion (ISA/KR) for International Application No. PCT/US2016/039092, dated Sep. 6, 2016.
International Search Report and Written Opinion (ISA/KR) for International Application No. PCT/US2016/062114, dated Mar. 9, 2017.
International Search Report and Written Opinion (ISA/US) for International Application No. PCT/US2016/021581, dated Jun. 2, 2016.
International Search Report and Written Opinion (ISA/US) for International Application No. PCT/US2016/025665, dated Sep. 8, 2016.
Jain, M. et al. (2004) "Sulfonyl-containing aldophosphamide analogues as novel anticancer prodrugs targeted against cyclophosphamide-resistant tumor cell lines," Journal of Medicinal Chemistry 47(15):3843-3852.
K. Misiura et al., "Stereospecific synthesis of chiral metabolites of Ifosfamide and their determination in the Urine", Journal of Medicinal Chemistry., vol. 26, 1983, pp. 674-679, XP002786859, Usamerican Chemical Society. Washington. ISSN: 0022-2623.
Li, Z. et al., "Nitrobenzocyclophosphamides as Potential Prodrugs for Bioreductive Activation: Synthesis, Stability, Enzymatic Reduction, and Antiproliferative Activity in Cell Culture", Bioorganic & Medicinal Chemistry, vol. 11, No. 19, 2003, pp. 4171-4178.
Mulcahy, R.T. et al. (1994) "Nitrobenzyl phosphorodiamidates as potential hypoxia-selective alkylating agents", Journal of Medicinal Chemistry 37:1610-1615.
NIH National Cancer Institute (2015) "Targeted Cancer Therapies Fact Sheet," see http://www.cancer.gov/about-cancer/treatment/types/targeted-therapies/targeted-therapies-fact-sheet, accessed Dec. 8, 2015.
Non-Final Office Action in U.S. Appl. No. 15/326,990, dated Apr. 30, 2018.
Non-Final Office Action in U.S. Appl. No. 15/557,053, dated Jun. 22, 2018.

(56) References Cited

OTHER PUBLICATIONS

Non-Final Office Action on U.S. Appl. No. 15/563,481 dated Nov. 16, 2018.
Non-Final Office Action on U.S. Appl. No. 15/736,285 dated Sep. 27, 2018.
Non-Final Office Action on U.S. Appl. No. 15/752,854 dated Nov. 20, 2018.
Notice of Allowance in U.S. Appl. No. 15/326,990, dated Jul. 5, 2018.
Notice of Allowance on U.S. Appl. No. 15/326,990 dated Oct. 15, 2018.
Notice of Allowance on U.S. Appl. No. 15/557,053 dated Apr. 22, 2019.
Notice of Allowance on U.S. Appl. No. 15/557,053 dated May 15, 2019.
Notice of Allowance on U.S. Appl. No. 15/557,053 dated Dec. 28, 2018.
Notice of Allowance on U.S. Appl. No. 15/736,285 dated Jan. 24, 2019.
Notice of Allowance on U.S. Appl. No. 15/752,854 dated Apr. 25, 2019.
Rastelli et al. Discovery of New Inhibitors of Aldose Reductase from Molecular Docking and Database Screening. Bioorganic & Medicinal Chemistry 10 (2002) 1437-1450. (Year: 2002).
Restriction Requirement in U.S. Appl. No. 15/563,481, dated Jul. 25, 2018.

* cited by examiner

AZIRIDINE CONTAINING DNA ALKYLATING AGENTS

CROSS-REFERENCE TO RELATED APPLICATION

This application is a continuation application of U.S. application Ser. No. 15/736,285, filed on Dec. 13, 2017, which claims priority under 35 U.S.C. § 371 of International Application No. PCT/US2016/039092, filed Jun. 23, 2016, which claims priority under 35 U.S.C. § 119(e) to U.S. Provisional Application No. 62/184,129, filed Jun. 24, 2015, the content of which is hereby incorporated by reference in its entirety.

FIELD OF INVENTION

The present invention provides compounds suitable as therapeutic agents, pharmaceutical compositions of such compounds and methods of treating cancer in cancer patients, and so relates to the fields of biology, chemistry, and medicine.

BACKGROUND OF THE INVENTION

Cancer is one of the major causes of human morbidity and mortality. Cancer treatment is challenging because it is difficult to kill cancer cells without damaging or killing normal cells. Damaging or killing normal cells during cancer treatment is a cause of adverse side effects in patients and can limit the amount of anti-cancer drug administered to a cancer patient. There remains a need for compounds suitable for treating cancer patients.

SUMMARY

In one aspect, In one aspect, provided herein are compounds selected from:

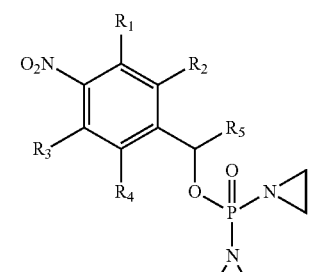

(I)

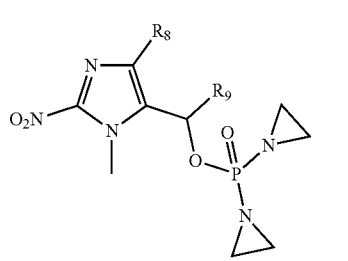

(II)

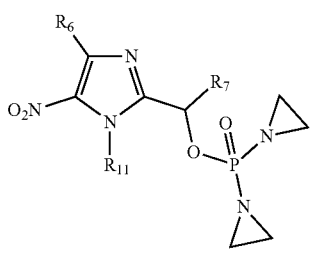

(III)

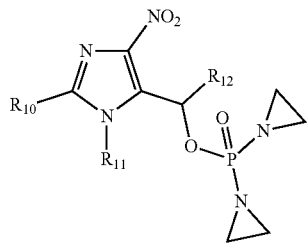

(IV)

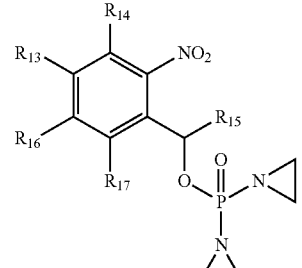

(V)

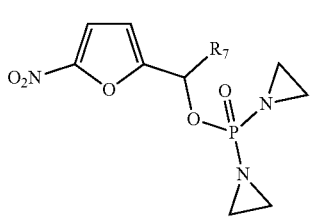

(VI)

wherein the variables are defined and illustrated herein below. As provided herein the compounds include mixtures of stereoisomers, such as enantiomers, and separated individual enantiomers and racemic and nonracemic mixtures thereof. Without being bound by theory, in certain embodiments, the compounds provided here act as prodrugs that can be activated in or around the hypoxic conditions existing in or around tumors.

In another aspect, provided herein are methods of preparing the compounds provided herein.

In another aspect, provided herein are pharmaceutical compositions comprising a compound provided herein and at least one pharmaceutically acceptable excipient.

In another aspect, provided herein are methods of treating cancer comprising administering to a patient in need thereof a therapeutically effective amount of a compound provided herein, or a therapeutically effective amount of a composition provided herein.

BRIEF DESCRIPTION OF FIGURES

The comparative tumor volume reductions for certain compounds are graphically illustrated in FIGS. 1A-1C.

DETAILED DESCRIPTION OF THE INVENTION

Definitions

Figure 1A:
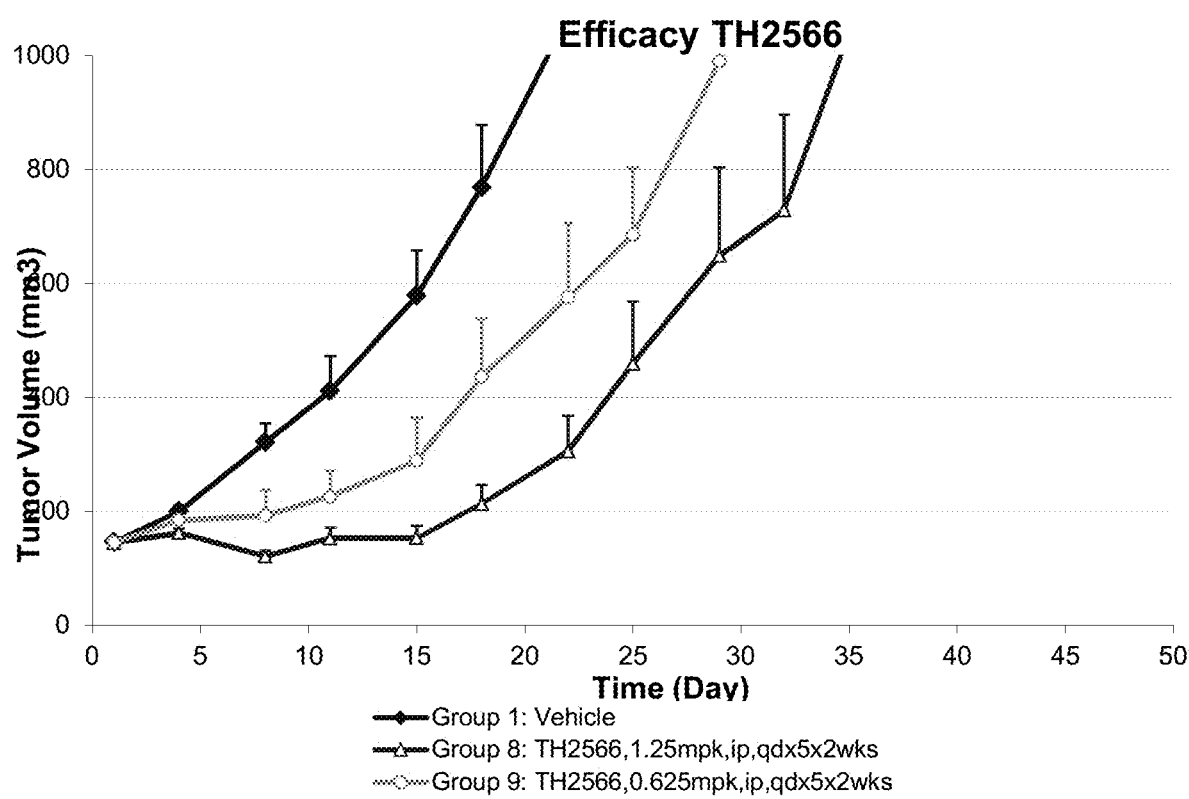

The following definitions are provided to assist the reader. Unless otherwise defined, all terms of art, notations, and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not be construed as representing a substantial difference over the definition of the term as generally understood in the art.

All numerical designations, e.g., pH, temperature, time, concentration, and weight, including ranges of each thereof, are approximations that typically may be varied (+) or (−) by increments of 0.1, 1.0, or 10.0, as appropriate. All numerical designations may be understood as preceded by the term "about". Reagents described herein are exemplary and equivalents of such may be known in the art.

"A," "an," and, "the" include plural referents unless the context clearly dictates otherwise. Thus, for example, reference to a compound refers to one or more compounds or at least one compound. As such, the terms "a" (or "an"), "one or more", and "at least one" are used interchangeably herein.

As used herein, the term "comprising" is intended to mean that the compositions and methods include the recited elements, but not excluding others. "Consisting essentially of" when used to define compositions and methods, shall mean excluding other elements of any essential significance to the composition or method. "Consisting of" shall mean excluding more than trace elements of other ingredients for claimed compositions and substantial method steps. Embodiments defined by each of these transition terms are within the scope of this invention. Accordingly, it is intended that the methods and compositions can include additional steps and components (comprising) or alternatively including steps and compositions of no significance (consisting essentially of) or alternatively, intending only the stated method steps or compositions (consisting of).

"$C_x$-$C_y$" or "$C_{x-y}$" before a group refers to a range of the number of carbon atoms that are present in that group. For example, $C_1$-$C_6$ alkyl refers to an alkyl group having at least 1 and up to 6 carbon atoms.

"Alkoxy" refers to —O-Alkyl.

"Amino" refers to $NR^pR^q$ wherein $R^p$ and $R^q$ independently are hydrogen or $C_1$-$C_6$ alklyl, or $R^p$ and $R^q$ together with the nitrogen atom they are bonded to form a 4-15 membered heterocycle.

"Alkyl" refers to monovalent saturated aliphatic hydrocarbyl groups having from 1 to 10 carbon atoms and, in some embodiments, from 1 to 6 carbon atoms. "$C_{x-y}$ alkyl" refers to alkyl groups having from x to y carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—).

"Alkenyl" refers to a linear or branched hydrocarbyl group having from 2 to 10 carbon atoms and in some embodiments from 2 to 6 carbon atoms or 2 to 4 carbon atoms and having at least 1 site of vinyl unsaturation (>C=C<). For example, $C_{x-y}$ alkenyl refers to alkenyl groups having from x to y carbon atoms and is meant to include, for example, ethenyl, propenyl, 1,3-butadienyl, and the like.

"Alkynyl" refers to a linear monovalent hydrocarbon radical or a branched monovalent hydrocarbon radical 2 to 10 carbon atoms and in some embodiments from 2 to 6 carbon atoms or 2 to 4 carbon atoms and containing at least one triple bond. The term "alkynyl" is also meant to include those hydrocarbyl groups having one triple bond and one double bond. For example, $C_{2-6}$ alkynyl includes ethynyl, propynyl, and the like.

"Aryl" refers to an aromatic group of from 6 to 14 carbon atoms and no ring heteroatoms and having a single ring (e.g., phenyl) or multiple condensed (fused) rings (e.g., naphthyl or anthryl). For multiple ring systems, including fused, bridged, and spiro ring systems having aromatic and non-aromatic rings that have no ring heteroatoms, the term "Aryl" or "Ar" applies when the point of attachment is at an aromatic carbon atom (e.g., 5,6,7,8 tetrahydronaphthalene-2-yl is an aryl group as its point of attachment is at the 2-position of the aromatic phenyl ring).

"Cycloalkyl" refers to a saturated or partially saturated cyclic group of from 3 to 14 carbon atoms and no ring heteroatoms and having a single ring or multiple rings including fused, bridged, and spiro ring systems. For multiple ring systems having aromatic and non-aromatic rings that have no ring heteroatoms, the term "cycloalkyl" applies when the point of attachment is at a non-aromatic carbon atom (e.g., 5,6,7,8,-tetrahydronaphthalene-5-yl). The term "cycloalkyl" includes cycloalkenyl groups. Examples of cycloalkyl groups include, for instance, adamantyl, cyclopropyl, cyclobutyl, cyclopentyl, cyclooctyl, and cyclohexenyl.

"Ether" refers to a $C_1$-$C_6$ alkyl group substituted with 1-3 $C_1$-$C_6$ alkoxy groups, wherein alkoxy refers to —O-alkyl.

"Halo" refers to one or more of fluoro, chloro, bromo, and iodo.

"Heteroaryl" refers to an aromatic group of from 1 to 14 carbon atoms and 1 to 6 heteroatoms selected from the group consisting of oxygen, nitrogen, and sulfur and includes single ring (e.g. imidazolyl-2-yl and imidazol5-yl) and multiple ring systems (e.g. imidazopyridyl, benzotriazolyl, benzimidazol-2-yl and benzimidazol-6-yl). For multiple ring systems, including fused, bridged, and spiro ring systems having aromatic and non-aromatic rings, the term "heteroaryl" applies if there is at least one ring heteroatom, and the point of attachment is at an atom of an aromatic ring (e.g., 1,2,3,4-tetrahydroquinolin-6-yl and 5,6,7,8-tetrahydroquinolin-3-yl). In some embodiments, the nitrogen and/or the sulfur ring atom(s) of the heteroaryl group are optionally oxidized to provide for the N-oxide (N→O), sulfinyl, or sulfonyl moieties. The term heteroaryl includes, but is not limited to, acridinyl, azocinyl, benzimidazolyl, benzofuranyl, benzothiofuranyl, benzothiophenyl, benzoxazolyl, benzothiazolyl, benzotriazolyl, benzotetrazolyl, benzisoxazolyl, benzisothiazolyl, benzothienyl, benzimidazolinyl, carbazolyl, NH-carbazolyl, carbolinyl, chromanyl, chromenyl, cinnolinyl, dithiazinyl, furanyl, furazanyl, imidazolidinyl, imidazolinyl, imidazopyridyl, imidazolyl, indazolyl, indolenyl, indolinyl, indolizinyl, indolyl, isobenzofuranyl, isochromanyl, isoindazolyl, isoindolinyl, isoindolyl, isoquinolinyl, isoquinolyl, isothiazolyl, isoxazolyl, naphthyridinyl, octahydroisoquinolinyl, oxadiazolyl, oxazolidinyl, oxazolyl, pyrimidinyl, phenanthridinyl, phenanthrolinyl, phenazinyl, phenothiazinyl, phenoxathiinyl, phenoxazinyl, phthalazinyl, piperazinyl, pteridinyl, purinyl, pyranyl, pyrazinyl, pyrazolidinyl, pyrazolinyl, pyrazolyl, pyridazinyl, pyridooxazolyl, pyridoimidazolyl, pyridothiazole, pyridinyl, pyridyl, pyrimidinyl, pyrrolyl, quinazolinyl, quinolinyl, quinoxalinyl, quinuclidinyl, tetrahydroisoquinolinyl, tetrahydroquinolinyl, tetrazolyl, thiadiazinyl, thiadiazolyl, thianthrenyl, thiazolyl, thienyl, thienothiazolyl, thienooxazolyl, thienoimidazolyl, thiophenyl, triazinyl and xanthenyl.

"Heterocyclic" or "heterocycle" or "heterocycloalkyl" or "heterocyclyl" refers to a saturated or partially saturated cyclic group having from 1 to 14 carbon atoms and from 1 to 6 heteroatoms selected from the group consisting of nitrogen, sulfur, or oxygen and includes single ring and multiple ring systems including fused, bridged, and spiro ring systems. For multiple ring systems having aromatic and/or non-aromatic rings, the terms "heterocyclic", "heterocycle", "heterocycloalkyl", or "heterocyclyl" apply when there is at least one ring heteroatom, and the point of attachment is at an atom of a non-aromatic ring (e.g., 1,2,3,4-tetrahydroquinoline-3-yl, 5,6,7,8-tetrahydroquinoline-6-yl, and decahydroquinolin-6-yl). In some embodiment, the heterocyclic groups herein are 3-15 membered, 4-14 membered, 5-13 membered, 7-12, or 5-7 membered heterocycles. In some other embodiment, the heterocycles contain 4 heteroatoms. In some other embodiment, the heterocycles contain 3 heteroatoms. In another embodiment, the heterocycles contain up to 2 heteroatoms. In some embodiments, the nitrogen and/or sulfur atom(s) of the heterocyclic group are optionally oxidized to provide for the N-oxide, sulfinyl, sulfonyl moieties. Heterocyclyl includes, but is not limited to, tetrahydropyranyl, piperidinyl, N-methylpiperidin-3-yl, piperazinyl, N-methylpyrrolidin-3-yl, 3-pyrrolidinyl, 2-pyrrolidon-1-yl, morpholinyl, and pyrrolidinyl. A prefix indicating the number of carbon atoms (e.g., $C_{3-10}$) refers to the total number of carbon atoms in the portion of the heterocyclyl group exclusive of the number of heteroatoms. A divalent heterocyclic radical will have the appropriately adjusted hydrogen content.

The term "optionally substituted" refers to a substituted or unsubstituted group. The group may be substituted with one or more substituents, such as e.g., 1, 2, 3, 4 or 5 substituents. Preferably, the substituents are selected from the group consisting of oxo, halo, —CN, $NO_2$, —$N_2$+, —$CO_2R^{100}$, —$OR^{100}$, —$SR^{100}$, —$SOR^{100}$, —$SO_2R^{100}$, —$NR^{100}SO_2R^{100}$, —$NR^{101}R^{102}$, —$CONR^{101}R^{102}$, —$SO_2NR^{101}R^{102}$, $C_1$-$C_6$ alkyl, $C_1$-$C_6$ alkoxy, —$CR^{100}$=C($R^{100}$)$_2$, —$CCR^{100}$, $C_3$-$C_{10}$ cycloalkyl, $C_3$-$C_{10}$ heterocyclyl, $C_6$-$C_{12}$ aryl and $C_2$-$C_{12}$ heteroaryl, or a divalent substituent such as —O—(CH$_2$)—O—, —O—(CH$_2$)$_2$—O—, and, 1-4 methyl substituted version thereof, wherein each $R^{100}$, $R^{101}$, and $R^{102}$ independently is hydrogen or $C_1$-$C_8$ alkyl; $C_3$-$C_{12}$ cycloalkyl; $C_3$-$C_{10}$ heterocyclyl; $C_6$-$C_{12}$ aryl; or $C_2$-$C_{12}$ heteroaryl; or $R^{101}$ and $R^{102}$ together with the nitrogen atom they are attached to form a 5-7 membered heterocycle; wherein each alkyl, cycloalkyl, heterocyclyl, aryl, or heteroaryl is optionally substituted with 1-3 halo, 1-3 $C_1$-$C_6$ alkyl, 1-3 $C_1$-$C_6$ haloalkyl or 1-3 $C_1$-$C_6$ alkoxy groups. Preferably, the substituents are selected from the group consisting of chloro, fluoro including trifluoro, —$OCH_3$, methyl, ethyl, iso-propyl, cyclopropyl, OH, OAc, 5-6 membered heterocyclyl containing 1-3 heteroatoms such as nitrogen and oxygen optionally substituted with 1-3 $C_1$-$C_6$ alkyl or $C_6$-$C_{10}$ aryl groups, 5-6 membered heteroaryl containing 1-3 heteroatoms such as nitrogen and oxygen optionally substituted with 1-3 $C_1$-$C_6$ alkyl groups, —$CO_2H$ and salts and $C_1$-$C_6$ alkyl esters thereof, $CONMe_2$, $CONHMe$, $CONH_2$, —$SO_2Me$, —$SO_2NH_2$, —$SO_2NMe_2$, —$SO_2NHMe$, —$NHSO_2Me$, —$NHSO_2CF_3$, —$NHSO_2CH_2Cl$, —$NO_2$, —$NH_2$, —$NMe_2$, —$OCF_3$, —$CF_3$ and —$OCHF_2$. Other optional substituents include those illustrated in the table herein below.

"Prodrug" refers to a compound that, after administration, is metabolized or otherwise converted to a biologically active or more active compound (or drug) with respect to at least one property. A prodrug, relative to the drug, is modified chemically in a manner that renders it, relative to the drug, less active or inactive, but the chemical modification is such that the corresponding drug is generated by metabolic or other biological processes after the prodrug is administered. A prodrug may have, relative to the active drug, altered metabolic stability or transport characteristics, fewer side effects or lower toxicity, or improved flavor (for example, see the reference Nogrady, 1985, Medicinal Chemistry A Biochemical Approach, Oxford University Press, New York, pages 388-392, incorporated herein by reference). A prodrug may be synthesized using reactants other than the corresponding drug.

"Administering" or "administration of" a drug to a patient (and grammatical equivalents of this phrase) refers to direct administration, which may be administration to a patient by a medical professional or may be self-administration, and/or indirect administration, which may be the act of prescribing a drug. For example, a physician who instructs a patient to self-administer a drug and/or provides a patient with a prescription for a drug is administering the drug to the patient.

"Cancer" refers to leukemias, lymphomas, carcinomas, and other malignant tumors, including solid tumors, of potentially unlimited growth that can expand locally by invasion and systemically by metastasis. Examples of cancers include, but are not limited to, cancer of the adrenal gland, bone, brain, breast, bronchi, colon and/or rectum, gallbladder, head and neck, kidneys, larynx, liver, lung, neural tissue, pancreas, prostate, parathyroid, skin, stomach, and thyroid. Certain other examples of cancers include, acute and chronic lymphocytic and granulocytic tumors, adenocarcinoma, adenoma, basal cell carcinoma, cervical dysplasia and in situ carcinoma, Ewing's sarcoma, epidermoid carcinomas, giant cell tumor, glioblastoma multiforma, hairy-cell tumor, intestinal ganglioneuroma, hyperplastic corneal nerve tumor, islet cell carcinoma, Kaposi's sarcoma, leiomyoma, leukemias, lymphomas, malignant carcinoid, malignant melanomas, malignant hypercalcemia, marfanoid habitus tumor, medullary carcinoma, metastatic skin carcinoma, mucosal neuroma, myeloma, mycosis fungoides, neuroblastoma, osteo sarcoma, osteogenic and other sarcoma, ovarian tumor, pheochromocytoma, polycythermia vera, primary brain tumor, small-cell lung tumor, squamous cell carcinoma of both ulcerating and papillary type, hyperplasia, seminoma, soft tissue sarcoma, retinoblastoma, rhabdomyosarcoma, renal cell tumor, topical skin lesion, veticulum cell sarcoma, and Wilm's tumor.

"Patient" and "subject" are used interchangeably to refer to a mammal in need of treatment for cancer. Generally, the patient is a human. Generally, the patient is a human diagnosed with cancer. In certain embodiments a "patient" or "subject" may refer to a non-human mammal used in screening, characterizing, and evaluating drugs and therapies, such as, a non-human primate, a dog, cat, rabbit, pig, mouse or a rat.

"Solid tumor" refers to solid tumors including, but not limited to, metastatic tumors in bone, brain, liver, lungs, lymph node, pancreas, prostate, skin and soft tissue (sarcoma).

"Therapeutically effective amount" of a drug refers to an amount of a drug that, when administered to a patient with cancer, will have the intended therapeutic effect, e.g., alleviation, amelioration, palliation or elimination of one or more manifestations of cancer in the patient. A therapeutic effect does not necessarily occur by administration of one dose, and may occur only after administration of a series of doses. Thus, a therapeutically effective amount may be administered in one or more administrations.

"Treating," "treatment of," or "therapy of" a condition or patient refers to taking steps to obtain beneficial or desired results, including clinical results. For purposes of this invention, beneficial or desired clinical results include, but are not limited to, alleviation or amelioration of one or more symptoms of cancer; diminishment of extent of disease; delay or slowing of disease progression; amelioration, palliation, or stabilization of the disease state; or other beneficial results. Treatment of cancer may, in some cases, result in partial response or stable disease.

Compounds

In one aspect, provided herein is a compound selected from:

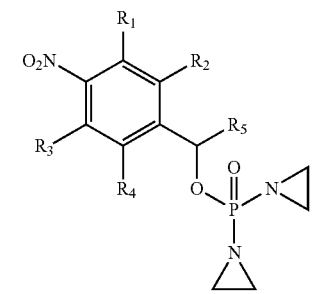
(I)

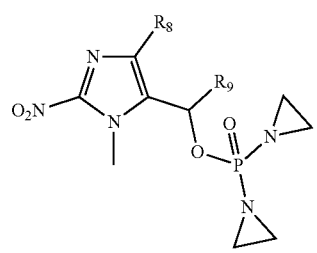
(II)

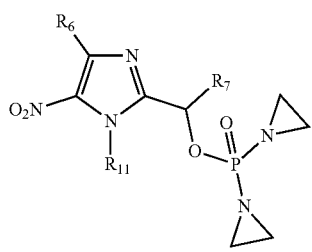
(III)

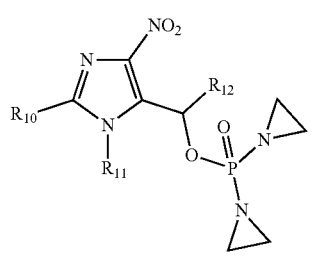
(IV)

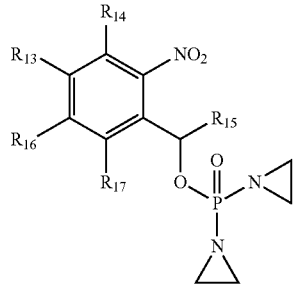
(V)

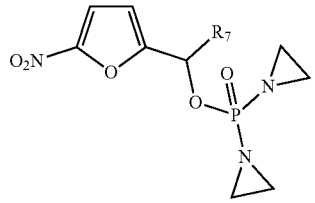
(VI)

or a pharmaceutically acceptable salt thereof, or a pharmaceutically acceptable solvate of each thereof, wherein $R^1$ is: hydrogen, —$N_3$, CN, halo, $NR^{21}R^{22}$, —$OR^{23}$, —$SO_2(C_1$-$C_6$ alkyl), $C_1$-$C_6$ alkyl, $C_2$-$C_6$ alkenyl, $C_2$-$C_6$ alkynyl, $C_3$-$C_5$ cycloalkyl, $C_6$-$C_{10}$ aryl, 4-15 membered heterocycle, 5-15 membered heteroaryl, or ether;

each $R^{21}$ and $R^{22}$ independently is hydrogen, hydroxy, $C_1$-$C_6$ alkyl, $C_2$-$C_6$ alkenyl, $C_2$-$C_6$ alkynyl, $C_3$-$C_5$ cycloalkyl, $C_6$-$C_{10}$ aryl, 4-15 membered heterocycle, 5-15 membered heteroaryl, or —$SO_2(C_1$-$C_6$ alkyl); or $R^{21}$ and $R^{22}$ together with the nitrogen atom they are bonded to form a 4-15 membered heterocycle or a 5-15 membered heteroaryl;

$R^{23}$ is hydrogen, $C_1$-$C_6$ alkyl, or $C_6$-$C_{10}$ aryl;

$R^2$ and $R^3$ are independently hydrogen or halo;

$R^4$ is hydrogen, halo, $C_1$-$C_6$ alkoxy, $C_1$-$C_6$ alkyl, or $C_6$-$C_{10}$ aryl, $R^5$, $R^7$, $R^9$, $R^{12}$, and $R^{15}$ independently are hydrogen, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl; or $R^4$ and $R^5$ together with the intervening carbon atoms between them form a $C_5$-$C_6$ cycloalkyl ring;

$R^6$ and $R^{10}$ independently are hydrogen or halo;

$R^8$ is hydrogen, $C_1$-$C_6$ alkyl, $C_2$-$C_6$ alkenyl, $C_2$-$C_6$ alkynyl, or 5-15 membered heteroaryl;

each $R^{11}$ independently is $C_1$-$C_6$ alkyl, $C_2$-$C_6$ alkenyl, $C_2$-$C_6$ alkynyl, $C_3$-$C_8$ cycloalkyl, or $C_6$-$C_{10}$ aryl;

$R^{13}$, $R^{14}$, $R^{16}$, and $R^{17}$ are independently hydrogen, halo, $C_1$-$C_6$ alkyl, $C_2$-$C_6$ alkenyl, $C_2$-$C_6$ alkyny, or $C_1$-$C_6$ alkoxy;

wherein the alkyl, alkenyl, alkynyl, cycloalkyl, aryl, heterocycle, heteroaryl, alkoxy and ether groups are optionally substituted.

In one embodiment, the compound provided is of formula:

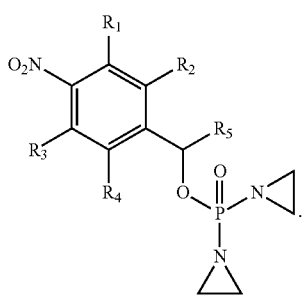

(I)

In another embodiment, $R^1$ is a non-hydrogen substituent. In another embodiment, $R^2$ and $R^3$ are hydrogen. In another embodiment, $R^4$ is hydrogen or halo. In another embodiment, $R^4$ is hydrogen. In another embodiment, $R^4$ is halo. In another embodiment, $R^4$ is fluoro. In another embodiment, $R^4$ and $R^5$ together form a 5 membered cycloalkyl group. In another embodiment, $R^1$ is a non-hydrogen substituent, $R^2$ and $R^3$ are hydrogen, and $R^4$ is hydrogen or halo, or $R^4$ and $R^5$ together form a 5 membered cycloalkyl group. In another embodiment, $R^5$ is a non-hydrogen substituent. In another embodiment, $R^1$ is $NR^{21}R^{22}$.

In another embodiment, the compound provided is of formula:

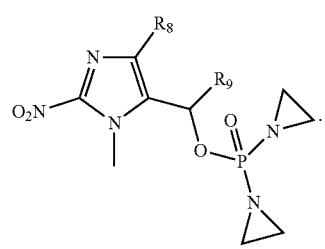

(II)

In another embodiment, $R^8$ is hydrogen. In another embodiment, $R^8$ is $C_1$-$C_6$ alkyl, $C_2$-$C_6$ alkenyl, or $C_2$-$C_6$ alkynyl. In another embodiment, $R^9$ is optionally substituted $C_1$-$C_6$ alkyl.

In another embodiment, the compound provided is of formula:

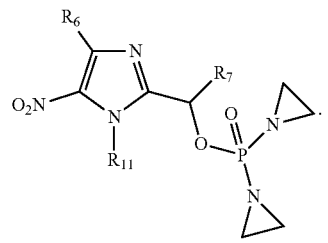

(III)

In another embodiment, $R^7$ is optionally substituted $C_1$-$C_6$ alkyl.

In another embodiment, the compound provided is of formula:

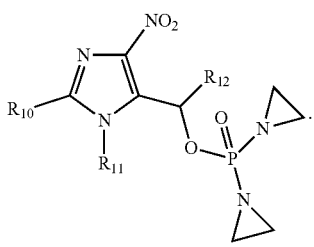

(IV)

In another embodiment, $R^{12}$ is optionally substituted $C_1$-$C_6$ alkyl.

In another embodiment, the compound provided is of formula:

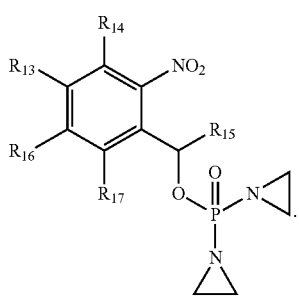

(V)

In another embodiment, $R^{15}$ is optionally substituted $C_1$-$C_6$ alkyl.

In another embodiment, the compound provided is of formula:

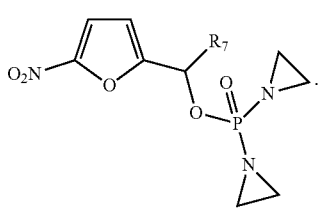

(VI)

In another embodiment, $R^7$ is optionally substituted $C_1$-$C_6$ alkyl.

Certain non-limiting and illustrative compounds provided and/or utilized herein are tabulated below along with their anti-cancer abilities under nitrogen and under air.

| compound | structure | IC$_{50}$ (N$_2$) μM | IC$_{50}$ (air) μM |
|---|---|---|---|
| 2118 | 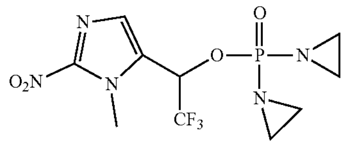 [SMILES: Cn1c(C(OP(=O)(N2CC2)N2CC2)C(F)(F)F)cnc1[N+](=O)[O-]] | 0.01 | 6.2 |
| 2119 | 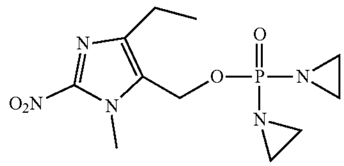 [SMILES: CCc1nc([N+](=O)[O-])n(C)c1COP(=O)(N1CC1)N1CC1] | 0.03 | 0.9 |
| 2127 | 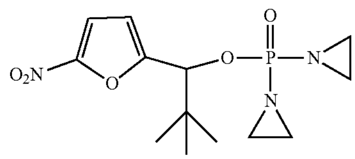 [SMILES: CC(C)(C)C(OP(=O)(N1CC1)N1CC1)c1ccc([N+](=O)[O-])o1] | 0.02 | 18 |
| 2128 | 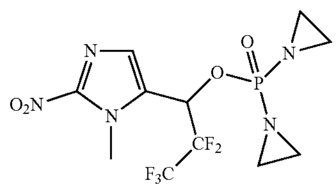 [SMILES: Cn1c(C(OP(=O)(N2CC2)N2CC2)C(F)(F)C(F)(F)F)cnc1[N+](=O)[O-]] | 0.02 | 18 |
| 2129 | 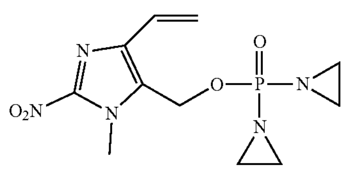 [SMILES: C=Cc1nc([N+](=O)[O-])n(C)c1COP(=O)(N1CC1)N1CC1] | 0.08 | 0.7 |
| 2130 | 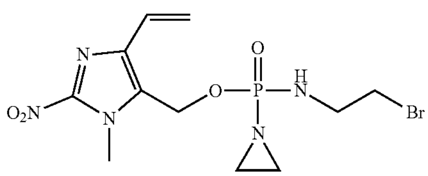 [SMILES: C=Cc1nc([N+](=O)[O-])n(C)c1COP(=O)(NCCBr)N1CC1] | 0.005 | 1.3 |
| 2136 | 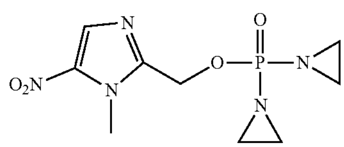 [SMILES: Cn1c([N+](=O)[O-])cnc1COP(=O)(N1CC1)N1CC1] | 0.1 | 24 |
| 2137 | 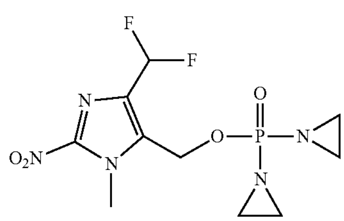 [SMILES: Cn1c([N+](=O)[O-])nc(C(F)F)c1COP(=O)(N1CC1)N1CC1] | 0.02 | 2.2 |
| 2138 | 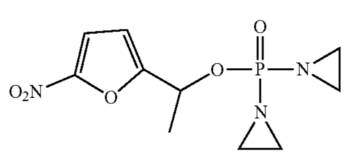 [SMILES: CC(OP(=O)(N1CC1)N1CC1)c1ccc([N+](=O)[O-])o1] | 0.006 | 0.3 |

-continued

| compound | structure | IC$_{50}$ (N$_2$) μM | IC$_{50}$ (air) μM |
| --- | --- | --- | --- |
| 2139 | 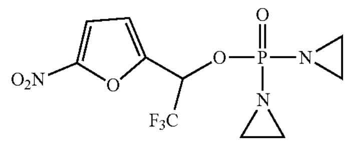 [SMILES: O=[N+]([O-])c1ccc(C(OP(=O)(N2CC2)N2CC2)C(F)(F)F)o1] | 0.004 | 0.3 |
| 2141 | 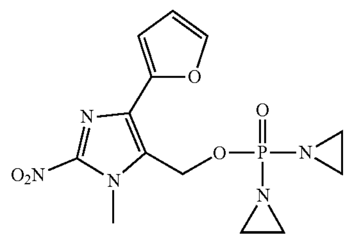 [SMILES: Cn1c([N+](=O)[O-])nc(-c2ccco2)c1COP(=O)(N1CC1)N1CC1] | 0.08 | 0.5 |
| 2145 | 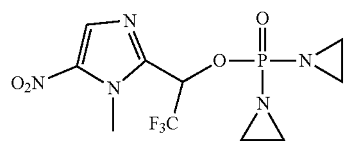 [SMILES: Cn1c([N+](=O)[O-])cnc1C(OP(=O)(N1CC1)N1CC1)C(F)(F)F] | 0.4 | 170 |
| 2147 | 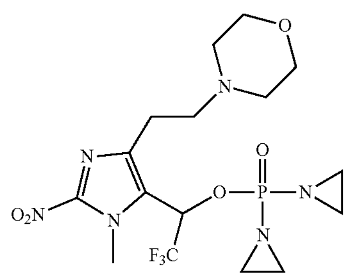 [SMILES: Cn1c([N+](=O)[O-])nc(CCN2CCOCC2)c1C(OP(=O)(N1CC1)N1CC1)C(F)(F)F] | 1.1 | 310 |
| 2149 | OR | 0.03 | 7.5 |
| 2151 | OR | 0.01 | 6 |

-continued

| compound | structure | IC$_{50}$ (N$_2$) μM | IC$_{50}$ (air) μM |
|---|---|---|---|
| 2334 | 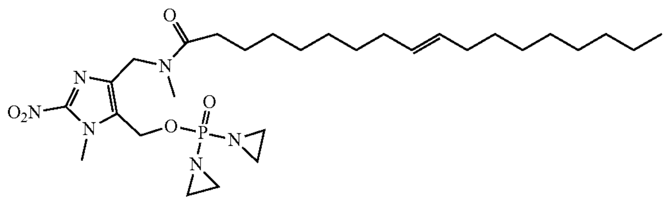 [SMILES: CCCCCCCC/C=C/CCCCCCCC(=O)N(C)Cc1nc([N+](=O)[O-])n(C)c1COP(=O)(N1CC1)N1CC1] | 0.009 | 0.14 |
| 2387 | 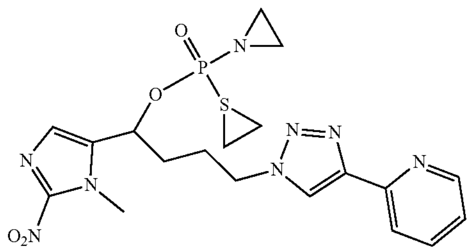 | 3.8 | 23 |
| 2501 | 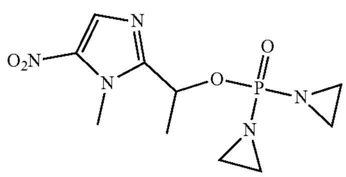 [SMILES: CC(OP(=O)(N1CC1)N1CC1)c1ncc([N+](=O)[O-])n1C] | 0.05 | 21 |
| 2518 | 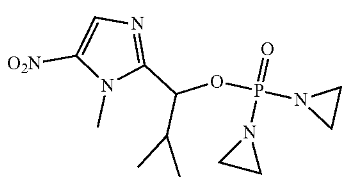 [SMILES: CC(C)C(OP(=O)(N1CC1)N1CC1)c1ncc([N+](=O)[O-])n1C] | 0.6 | 420 |
| 2519 | 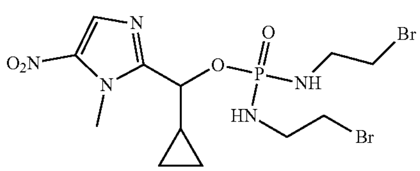 [SMILES: Cn1c([N+](=O)[O-])cnc1C(OP(=O)(NCCBr)NCCBr)C1CC1] | >500 | >500 |
| 2520 | 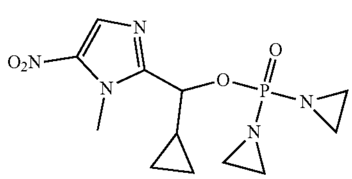 [SMILES: Cn1c([N+](=O)[O-])cnc1C(OP(=O)(N1CC1)N1CC1)C1CC1] | 8.8 | 20 |
| 2523 | 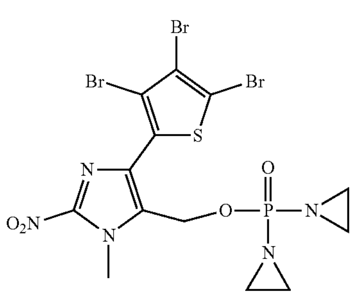 [SMILES: Cn1c([N+](=O)[O-])nc(-c2sc(Br)c(Br)c2Br)c1COP(=O)(N1CC1)N1CC1] | 0.02 | 0.4 |

-continued

| compound | structure | IC$_{50}$ (N$_2$) μM | IC$_{50}$ (air) μM |
|---|---|---|---|
| 2525 | 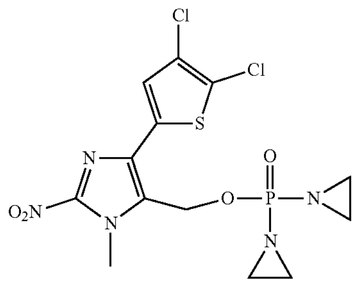 [SMILES: Cn1c([N+](=O)[O-])nc(-c2cc(Cl)c(Cl)s2)c1COP(=O)(N1CC1)N1CC1] | 0.02 | 0.7 |
| 2527 | 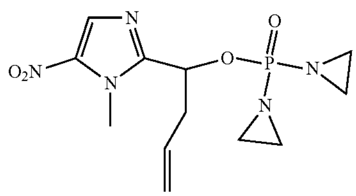 [SMILES: C=CCC(OP(=O)(N1CC1)N1CC1)c1ncc([N+](=O)[O-])n1C] | 0.09 | 39 |
| 2529 | 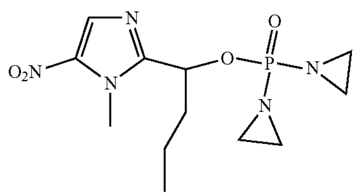 [SMILES: CCCC(OP(=O)(N1CC1)N1CC1)c1ncc([N+](=O)[O-])n1C] | 0.2 | 33 |
| 2535 | 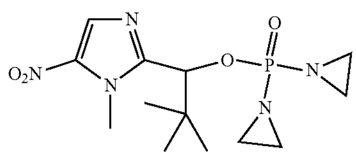 [SMILES: Cn1c([N+](=O)[O-])cnc1C(OP(=O)(N1CC1)N1CC1)C(C)(C)C] | 26 | 500 |
| 2537 | 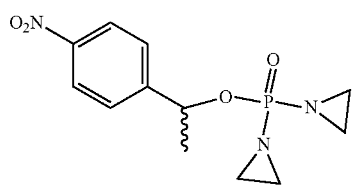 [SMILES: CC(OP(=O)(N1CC1)N1CC1)c1ccc([N+](=O)[O-])cc1] | 0.3 | 53 |
| 2542 | 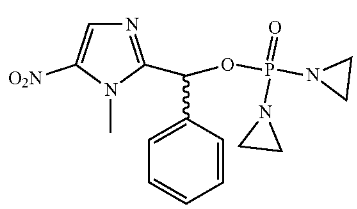 [SMILES: Cn1c([N+](=O)[O-])cnc1C(OP(=O)(N1CC1)N1CC1)c1ccccc1] | 1.5 | 3.4 |
| 2544 | 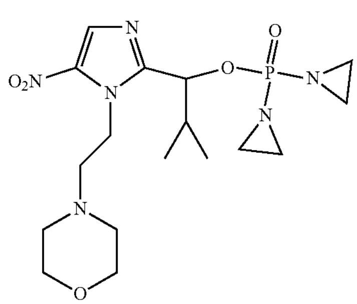 [SMILES: CC(C)C(OP(=O)(N1CC1)N1CC1)c1ncc([N+](=O)[O-])n1CCN1CCOCC1] | 0.2 | 45 |

-continued

| compound | structure | IC$_{50}$ (N$_2$) μM | IC$_{50}$ (air) μM |
|---|---|---|---|
| 2547 | 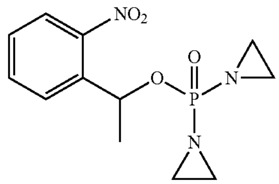 [SMILES: CC(OP(=O)(N1CC1)N1CC1)c1ccccc1[N+](=O)[O-]] | 2.6 | 320 |
| 2550 | 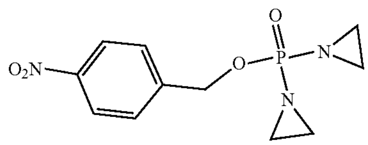 [SMILES: O=[N+]([O-])c1ccc(COP(=O)(N2CC2)N2CC2)cc1] | 1.8 | 29 |
| 2551 | (I) | 0.1 | 20 |
| 2552 | (II) | 0.1 | 23 |
| 2554 | 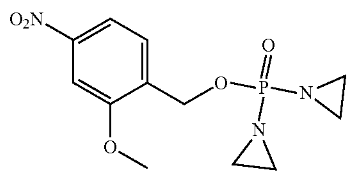 [SMILES: COc1cc([N+](=O)[O-])ccc1COP(=O)(N1CC1)N1CC1] | 0.1 | 3 |
| 2556 | 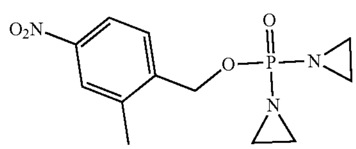 [SMILES: Cc1cc([N+](=O)[O-])ccc1COP(=O)(N1CC1)N1CC1] | 0.7 | 17 |
| 2560 | 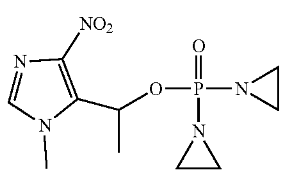 [SMILES: CC(OP(=O)(N1CC1)N1CC1)c1c([N+](=O)[O-])ncn1C] | 3.7 | 40 |
| 2561 | 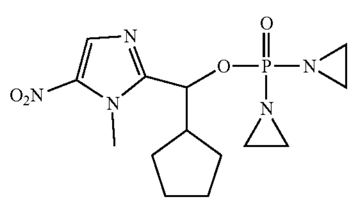 [SMILES: Cn1c([N+](=O)[O-])cnc1C(OP(=O)(N1CC1)N1CC1)C1CCCC1] | 0.2 | 29 |
| 2563 | 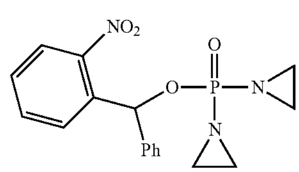 [SMILES: O=[N+]([O-])c1ccccc1C(OP(=O)(N1CC1)N1CC1)c1ccccc1] | 3.2 | 15 |

-continued

| compound | structure | IC$_{50}$ (N$_2$) μM | IC$_{50}$ (air) μM |
|---|---|---|---|
| 2565 | I | 0.1 | 18 |
| 2566 | II | 0.1 | 23 |
| 2567 | I | 0.3 | 270 |
| 2568 | II | 0.3 | 350 |
| 2569 | 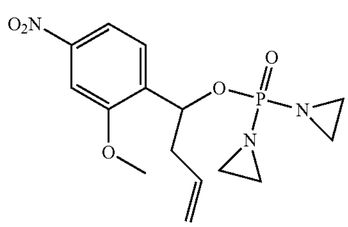 | 0.05 | 2 |
| 2572 | 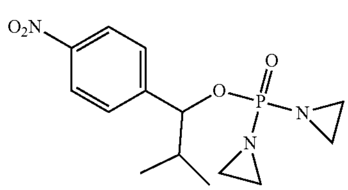 | 1.6 | 29 |
| 2574 | 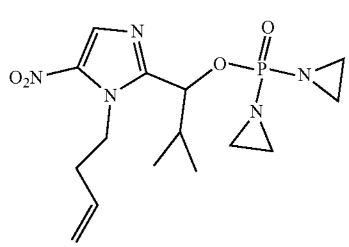 | 0.1 | 29 |

-continued

| compound | structure | IC$_{50}$ (N$_2$) μM | IC$_{50}$ (air) μM |
|---|---|---|---|
| 2576 | 4-nitro-2-chlorobenzyl N,N'-diaziridinyl phosphoramidate | 0.1 | 1.8 |
| 2578 | 2-nitrobenzyl N,N'-diaziridinyl phosphoramidate | 6 | 28 |
| 2579 | 4-nitro-3-chlorobenzyl N,N'-diaziridinyl phosphoramidate | 1.3 | 2.6 |
| 2580 | 4-nitro-3-methylbenzyl N,N'-diaziridinyl phosphoramidate | 3.7 | 20 |
| 2582 | (1-(but-3-enyl)-5-nitro-1H-imidazol-2-yl)methyl N,N'-diaziridinyl phosphoramidate | 0.1 | 18 |
| 2588 | 2-nitro-6-methylbenzyl N,N'-diaziridinyl phosphoramidate | 1.3 | 10 |
| 2589 | 4-methoxy-2-nitrobenzyl N,N'-diaziridinyl phosphoramidate | 0.1 | 9.6 |
| 2590 | 4-methyl-2-nitrobenzyl N,N'-diaziridinyl phosphoramidate | 2.9 | 15 |

-continued

| compound | structure | IC$_{50}$ (N$_2$) μM | IC$_{50}$ (air) μM |
|---|---|---|---|
| 2591 | 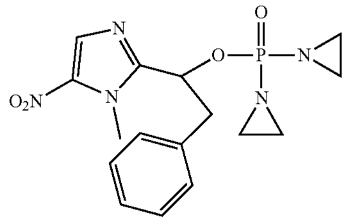 [SMILES: Cn1c([N+](=O)[O-])cnc1C(Cc1ccccc1)OP(=O)(N1CC1)N1CC1] | 0.1 | 19 |
| 2592 | 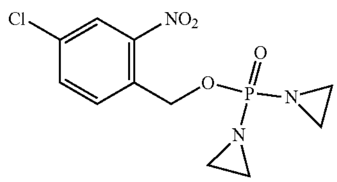 [SMILES: O=[N+]([O-])c1cc(Cl)ccc1COP(=O)(N1CC1)N1CC1] | 0.7 | 3.3 |
| 2594 | 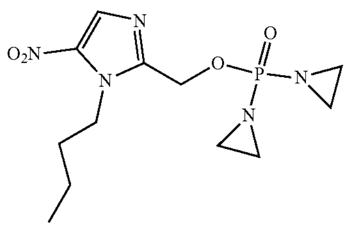 [SMILES: CCCCn1c([N+](=O)[O-])cnc1COP(=O)(N1CC1)N1CC1] | 0.15 | 7.4 |
| 2595 | 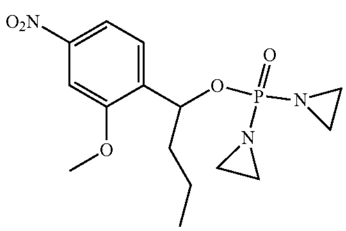 [SMILES: CCCC(OP(=O)(N1CC1)N1CC1)c1ccc([N+](=O)[O-])cc1OC] | 0.2 | 3.2 |
| 2599 | 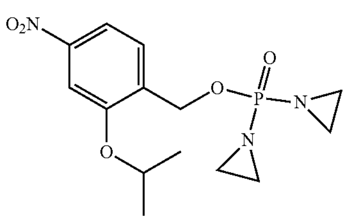 [SMILES: CC(C)Oc1cc([N+](=O)[O-])ccc1COP(=O)(N1CC1)N1CC1] | 0.08 | 1.5 |
| 2600 | 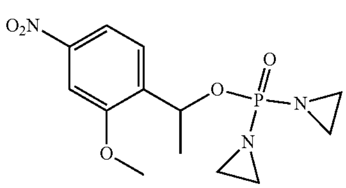 [SMILES: COc1cc([N+](=O)[O-])ccc1C(C)OP(=O)(N1CC1)N1CC1] | 0.05 | 2.8 |
| 2602 | 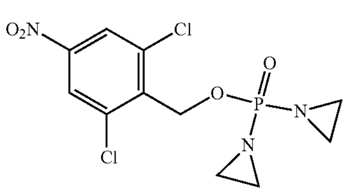 [SMILES: O=[N+]([O-])c1cc(Cl)c(COP(=O)(N2CC2)N2CC2)c(Cl)c1] | 0.02 | 0.25 |

-continued

| compound | structure | IC$_{50}$ (N$_2$) µM | IC$_{50}$ (air) µM |
|---|---|---|---|
| 2603 | 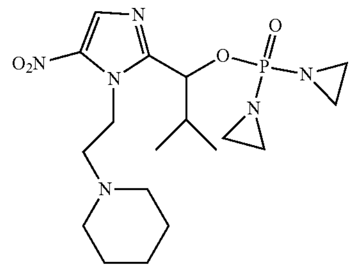 [SMILES: CC(C)C(OP(=O)(N1CC1)N1CC1)c1ncc([N+](=O)[O-])n1CCN1CCCCC1] | 0.3 | 29 |
| 2604 | 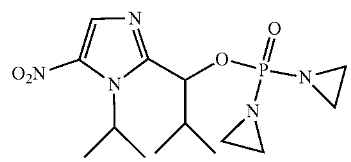 [SMILES: CC(C)C(OP(=O)(N1CC1)N1CC1)c1ncc([N+](=O)[O-])n1C(C)C] | 0.7 | 320 |
| 2608 | 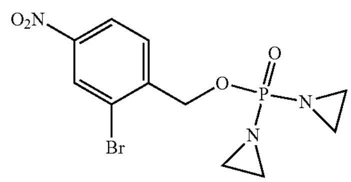 [SMILES: O=[N+]([O-])c1ccc(COP(=O)(N2CC2)N2CC2)c(Br)c1] | 0.3 | 3.1 |
| 2609 | 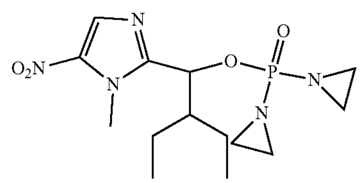 [SMILES: CCC(CC)C(OP(=O)(N1CC1)N1CC1)c1ncc([N+](=O)[O-])n1C] | 0.4 | 370 |
| 2610 | 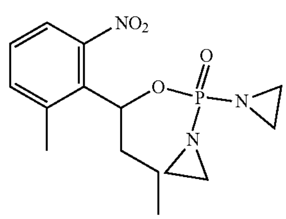 [SMILES: CCCC(OP(=O)(N1CC1)N1CC1)c1c(C)cccc1[N+](=O)[O-]] | 51 | 350 |
| 2611 | 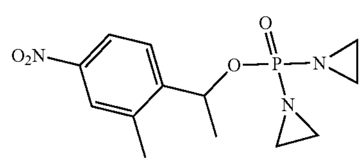 [SMILES: Cc1cc([N+](=O)[O-])ccc1C(C)OP(=O)(N1CC1)N1CC1] | 0.2 | 14 |
| 2613 | 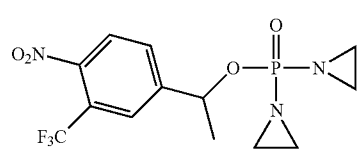 [SMILES: CC(OP(=O)(N1CC1)N1CC1)c1ccc([N+](=O)[O-])c(C(F)(F)F)c1] | 0.3 | 26 |
| 2615 | 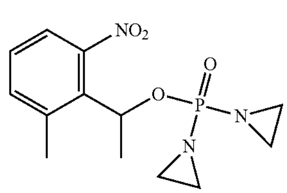 [SMILES: Cc1cccc([N+](=O)[O-])c1C(C)OP(=O)(N1CC1)N1CC1] | 320 | 350 |

-continued

| compound | structure | IC$_{50}$ (N$_2$) μM | IC$_{50}$ (air) μM |
| --- | --- | --- | --- |
| 2616 | 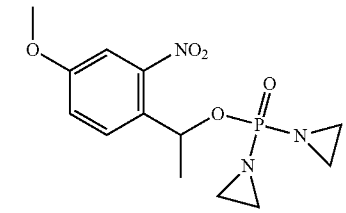 [SMILES: COc1ccc(C(C)OP(=O)(N2CC2)N2CC2)c([N+](=O)[O-])c1] | 3.7 | 17 |
| 2619 | 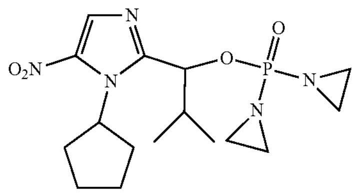 [SMILES: CC(C)C(OP(=O)(N1CC1)N1CC1)c1ncc([N+](=O)[O-])n1C1CCCC1] | 2.3 | 99 |
| 2620 | 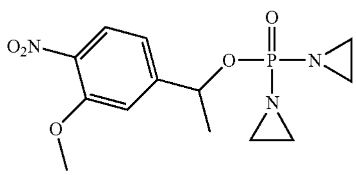 [SMILES: COc1cc(C(C)OP(=O)(N2CC2)N2CC2)ccc1[N+](=O)[O-]] | 2.5 | 7.4 |
| 2621 | 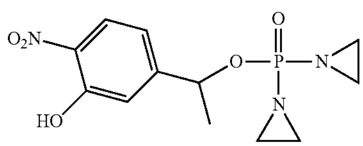 [SMILES: CC(OP(=O)(N1CC1)N1CC1)c1ccc([N+](=O)[O-])c(O)c1] | 0.3 | 39 |
| 2624 | 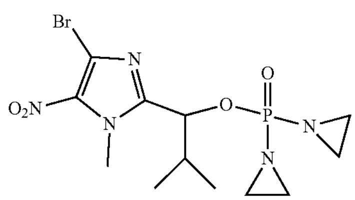 [SMILES: CC(C)C(OP(=O)(N1CC1)N1CC1)c1nc(Br)c([N+](=O)[O-])n1C] | 0.5 | 160 |
| 2626 | 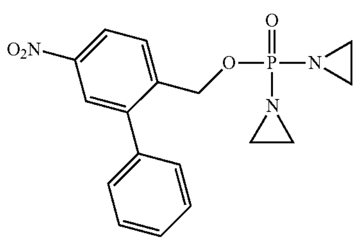 [SMILES: O=[N+]([O-])c1ccc(COP(=O)(N2CC2)N2CC2)c(-c2ccccc2)c1] | 0.6 | 3.3 |
| 2627 | 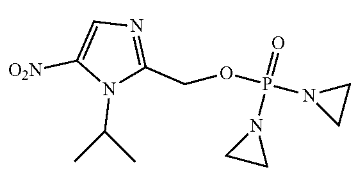 [SMILES: CC(C)n1c([N+](=O)[O-])cnc1COP(=O)(N1CC1)N1CC1] | 0.5 | 32 |
| 2633 | 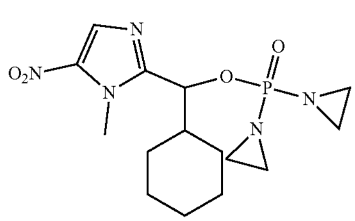 [SMILES: Cn1c([N+](=O)[O-])cnc1C(OP(=O)(N1CC1)N1CC1)C1CCCCC1] | 0.3 | 83 |

-continued

| compound | structure | IC$_{50}$ (N$_2$) μM | IC$_{50}$ (air) μM |
|---|---|---|---|
| 2635 | 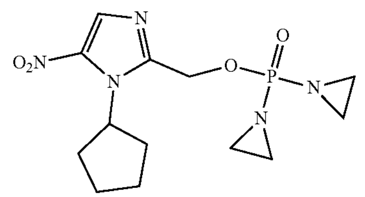 [SMILES: O=[N+]([O-])c1cnc(COP(=O)(N2CC2)N2CC2)n1C1CCCC1] | 0.22 | 13 |
| 2637 | 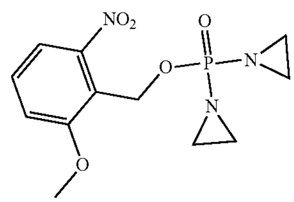 [SMILES: COc1cccc([N+](=O)[O-])c1COP(=O)(N1CC1)N1CC1] | 0.8 | 23 |
| 2640 | 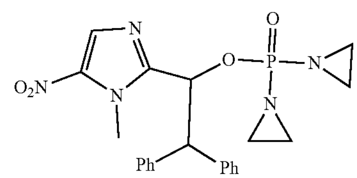 [SMILES: Cn1c([N+](=O)[O-])cnc1C(OP(=O)(N1CC1)N1CC1)C(c1ccccc1)c1ccccc1] | 1.1 | 83 |
| 2643 | 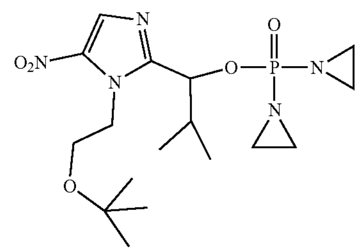 [SMILES: CC(C)C(OP(=O)(N1CC1)N1CC1)c1ncc([N+](=O)[O-])n1CCOC(C)(C)C] | 0.6 | 37 |
| 2645 | 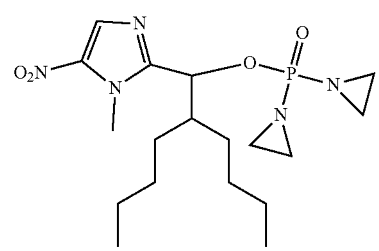 [SMILES: CCCCC(CCCC)C(OP(=O)(N1CC1)N1CC1)c1ncc([N+](=O)[O-])n1C] | 1.6 | 30 |
| 2652 | 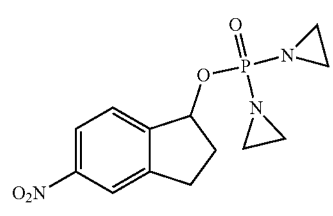 [SMILES: O=[N+]([O-])c1ccc2c(c1)CCC2OP(=O)(N1CC1)N1CC1] | 0.02 | 2.2 |
| 2654 | 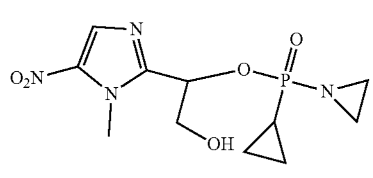 [SMILES: Cn1c([N+](=O)[O-])cnc1C(CO)OP(=O)(C1CC1)N1CC1] | 260 | >500 |

-continued

| compound | structure | IC$_{50}$ (N$_2$) μM | IC$_{50}$ (air) μM |
|---|---|---|---|
| 2656 | 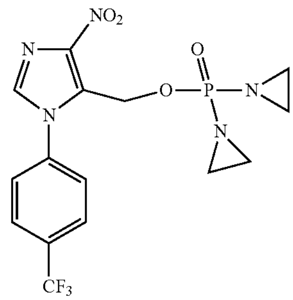 [SMILES: O=[N+]([O-])c1ncn(-c2ccc(C(F)(F)F)cc2)c1COP(=O)(N1CC1)N1CC1] | 0.1 | 2.4 |
| 2658 | 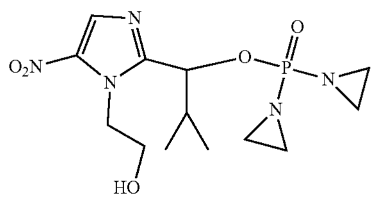 [SMILES: CC(C)C(OP(=O)(N1CC1)N1CC1)c1ncc([N+](=O)[O-])n1CCO] | 0.3 | 86 |
| 2662 | 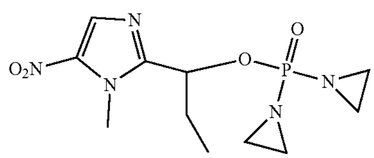 [SMILES: CCC(OP(=O)(N1CC1)N1CC1)c1ncc([N+](=O)[O-])n1C] | 0.03 | 22 |
| 2664 | 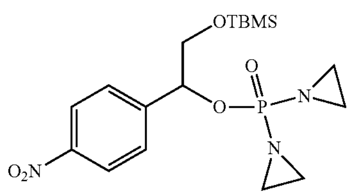 | 0.4 | 0.6 |
| 2666 | 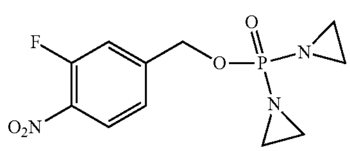 [SMILES: O=[N+]([O-])c1ccc(COP(=O)(N2CC2)N2CC2)cc1F] | 2 | 24 |
| 2672 | 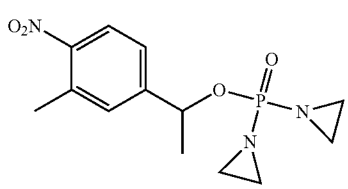 [SMILES: Cc1cc(C(C)OP(=O)(N2CC2)N2CC2)ccc1[N+](=O)[O-]] | 3.1 | 180 |
| 2675 | 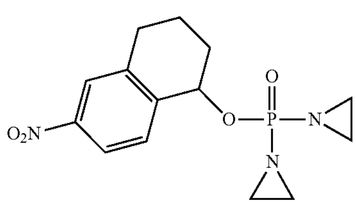 [SMILES: O=[N+]([O-])c1ccc2c(c1)CCCC2OP(=O)(N1CC1)N1CC1] | 0.05 | 3.4 |
| 2676 | 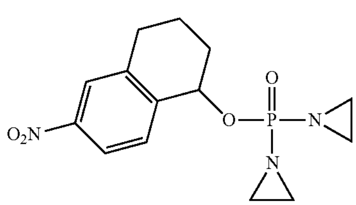 [SMILES: O=[N+]([O-])c1ccc2c(c1)CCCC2OP(=O)(N1CC1)N1CC1] | 0.1 | 3.7 |

-continued
| compound | structure | IC$_{50}$ (N$_2$) μM | IC$_{50}$ (air) μM |
|---|---|---|---|
| 2678 | 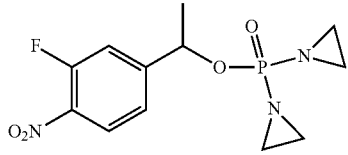 [SMILES: CC(OP(=O)(N1CC1)N1CC1)c1ccc([N+](=O)[O-])c(F)c1] | 0.4 | 32 |
| 2679 | 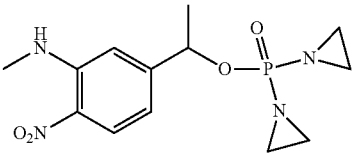 [SMILES: CNc1cc(C(C)OP(=O)(N2CC2)N2CC2)ccc1[N+](=O)[O-]] | 2.9 | 34 |
| 2680 | 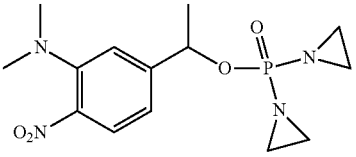 [SMILES: CC(OP(=O)(N1CC1)N1CC1)c1ccc([N+](=O)[O-])c(N(C)C)c1] | 2.6 | 110 |
| 2681 | 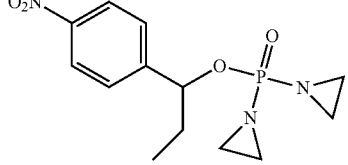 | 0.3 | 28 |
| 2686 | 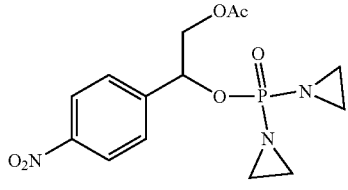 [SMILES: CC(=O)OCC(OP(=O)(N1CC1)N1CC1)c1ccc([N+](=O)[O-])cc1] | 3.1 | 79 |
| 2687 | 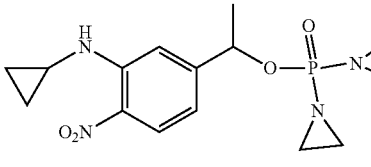 | 2.2 | 15 |
| 2689 | 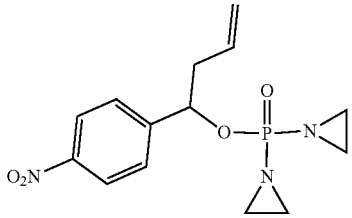 [SMILES: C=CCC(OP(=O)(N1CC1)N1CC1)c1ccc([N+](=O)[O-])cc1] | 0.6 | 43 |
| 2690 | 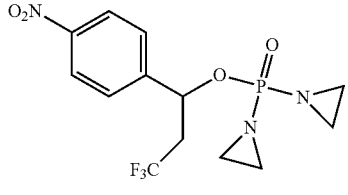 [SMILES: O=[N+]([O-])c1ccc(C(CC(F)(F)F)OP(=O)(N2CC2)N2CC2)cc1] | 3.2 | 99 |

-continued

| compound | structure | IC$_{50}$ (N$_2$) μM | IC$_{50}$ (air) μM |
| --- | --- | --- | --- |
| 2691 | 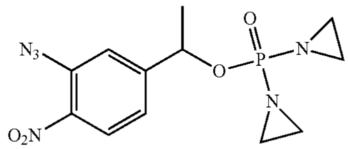 [SMILES: CC(OP(=O)(N1CC1)N1CC1)c1ccc([N+](=O)[O-])c(N=[N+]=[N-])c1] | 2.3 | 2.3 |
| 2692 | 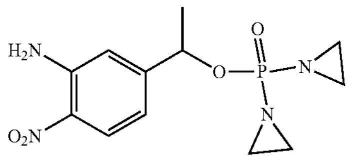 [SMILES: CC(OP(=O)(N1CC1)N1CC1)c1ccc([N+](=O)[O-])c(N)c1] | 2.7 | 6.2 |
| 2693 | 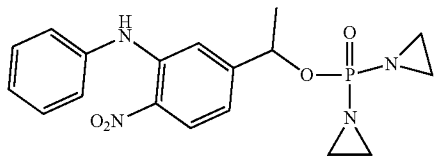 [SMILES: CC(OP(=O)(N1CC1)N1CC1)c1ccc([N+](=O)[O-])c(Nc2ccccc2)c1] | 0.4 | 1.9 |
| 2695 | 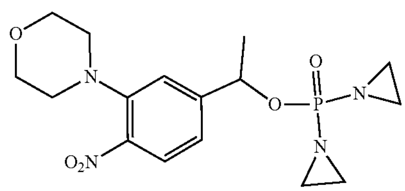 [SMILES: CC(OP(=O)(N1CC1)N1CC1)c1ccc([N+](=O)[O-])c(N2CCOCC2)c1] | 4.2 | 130 |
| 2696 | 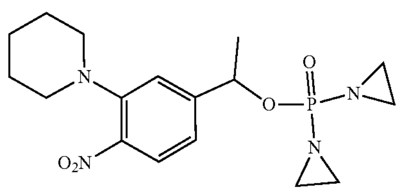 [SMILES: CC(OP(=O)(N1CC1)N1CC1)c1ccc([N+](=O)[O-])c(N2CCCCC2)c1] | 7.4 | 310 |
| 2697 | 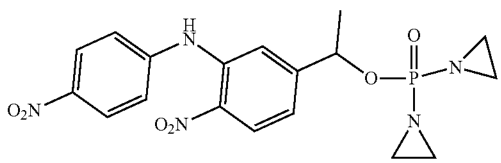 [SMILES: CC(OP(=O)(N1CC1)N1CC1)c1ccc([N+](=O)[O-])c(Nc2ccc([N+](=O)[O-])cc2)c1] | 0.5 | 1.5 |
| 2698 | 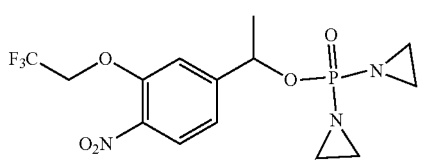 [SMILES: CC(OP(=O)(N1CC1)N1CC1)c1ccc([N+](=O)[O-])c(OCC(F)(F)F)c1] | 1.6 | 3.7 |
| 2700 | 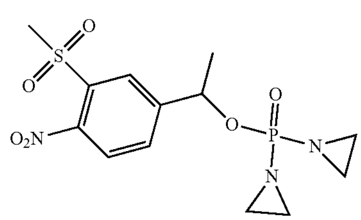 [SMILES: CC(OP(=O)(N1CC1)N1CC1)c1ccc([N+](=O)[O-])c(S(C)(=O)=O)c1] | 350 | 370 |
| 2701 | 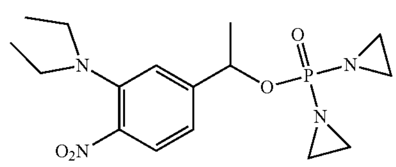 [SMILES: CCN(CC)c1cc(C(C)OP(=O)(N2CC2)N2CC2)ccc1[N+](=O)[O-]] | 1.3 | 66 |

-continued

| compound | structure | IC$_{50}$ (N$_2$) μM | IC$_{50}$ (air) μM |
| --- | --- | --- | --- |
| 2702 | 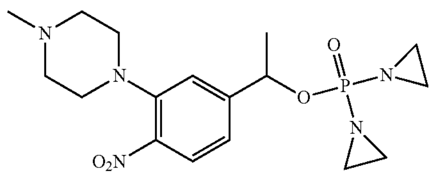 [SMILES: CC(OP(=O)(N1CC1)N1CC1)c1ccc([N+](=O)[O-])c(N2CCN(C)CC2)c1] | 0.8 | 47 |
| 2703 | 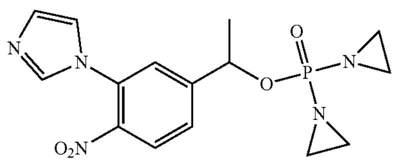 [SMILES: CC(OP(=O)(N1CC1)N1CC1)c1ccc([N+](=O)[O-])c(-n2ccnc2)c1] | 0.2 | 99 |
| 2706 | 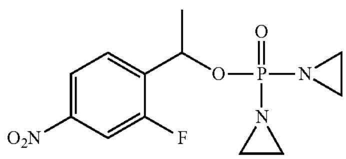 [SMILES: CC(OP(=O)(N1CC1)N1CC1)c1ccc([N+](=O)[O-])cc1F] | 0.03 | 14 |
| 2707 | 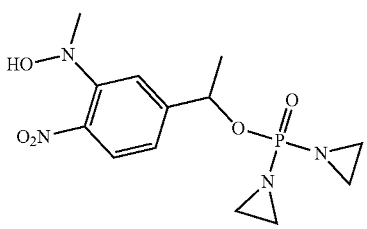 [SMILES: CC(OP(=O)(N1CC1)N1CC1)c1ccc([N+](=O)[O-])c(N(C)O)c1] | 0.1 | 0.2 |
| 2708 | 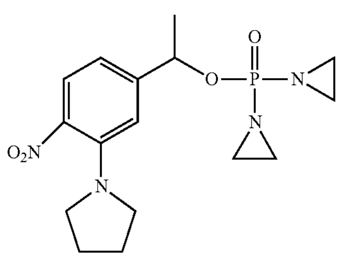 [SMILES: CC(OP(=O)(N1CC1)N1CC1)c1ccc([N+](=O)[O-])c(N2CCCC2)c1] | 3 | 20 |
| 2709 | 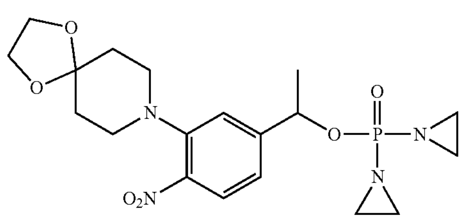 [SMILES: CC(OP(=O)(N1CC1)N1CC1)c1ccc([N+](=O)[O-])c(N2CCC3(CC2)OCCO3)c1] | 2.4 | 26 |
| 2710 | 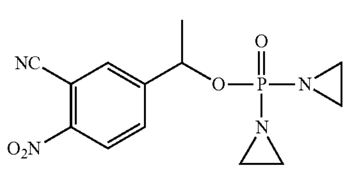 [SMILES: CC(OP(=O)(N1CC1)N1CC1)c1ccc([N+](=O)[O-])c(C#N)c1] | 0.03 | 3 |

-continued

| compound | structure | IC$_{50}$ (N$_2$) µM | IC$_{50}$ (air) µM |
|---|---|---|---|
| 2712 | *4-nitrophenyl with OTBDMS propyl chain, O-P(=O)(N-aziridinyl)$_2$* | 0.2 | 0.3 |
| 2714 | *4-nitrophenyl with OH propyl chain, O-P(=O)(N-aziridinyl)$_2$* | 0.5 | 94 |
| 2721 | *2,5-difluoro-4-nitrophenyl ethyl, O-P(=O)(N-aziridinyl)$_2$* | 0.02 | 9 |
| 2722 | *3-(2-methyl-4,5-dihydroimidazol-1-yl)-4-nitrophenyl ethyl, O-P(=O)(N-aziridinyl)$_2$* | 0.9 | 5 |
| 2723 | *3-(2-hydroxy-2-methylimidazolidin-1-yl)-4-nitrophenyl ethyl, O-P(=O)(N-aziridinyl)$_2$* | 29 | 420 |
| 2726 | *3-(methanesulfonamido)-4-nitrophenyl ethyl, O-P(=O)(N-aziridinyl)$_2$* | 0.2 | 19 |
| 2727 | *3-(1,2,4-triazol-1-yl)-4-nitrophenyl ethyl, O-P(=O)(N-aziridinyl)$_2$* | 0.2 | 31 |

-continued

| compound | structure | IC$_{50}$ (N$_2$) μM | IC$_{50}$ (air) μM |
|---|---|---|---|
| 2728 | 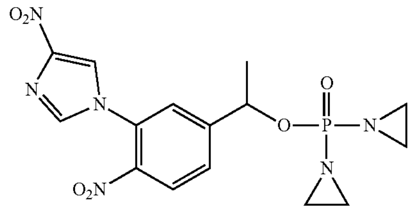 [SMILES: CC(OP(=O)(N1CC1)N1CC1)c1ccc([N+](=O)[O-])c(-n2cnc([N+](=O)[O-])c2)c1] | 0.2 | 22 |
| 2730 | 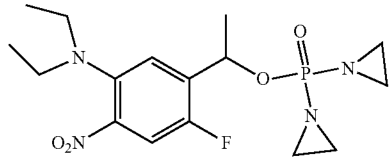 [SMILES: CCN(CC)c1cc(C(C)OP(=O)(N2CC2)N2CC2)c(F)cc1[N+](=O)[O-]] | 0.7 | 22 |
| 2731 | 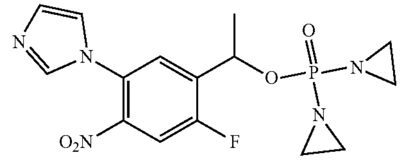 [SMILES: CC(OP(=O)(N1CC1)N1CC1)c1cc(-n2ccnc2)c([N+](=O)[O-])cc1F] | 0.1 | 13 |
| 2732 | 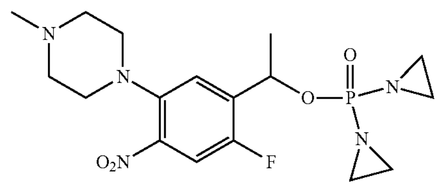 [SMILES: CC(OP(=O)(N1CC1)N1CC1)c1cc(N2CCN(C)CC2)c([N+](=O)[O-])cc1F] | 0.2 | 23 |
| 2733 | 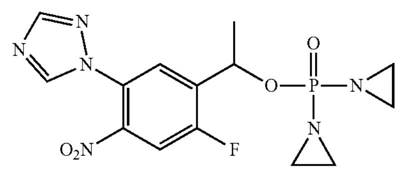 [SMILES: CC(OP(=O)(N1CC1)N1CC1)c1cc(-n2cncn2)c([N+](=O)[O-])cc1F] | 0.03 | 2.8 |
| 2734 | 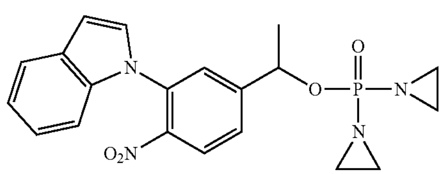 [SMILES: CC(OP(=O)(N1CC1)N1CC1)c1ccc([N+](=O)[O-])c(-n2ccc3ccccc32)c1] | 1.6 | 2.5 |
| 2735 | 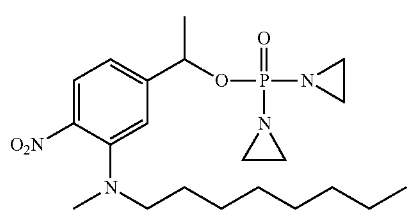 [SMILES: CCCCCCCCN(C)c1cc(C(C)OP(=O)(N2CC2)N2CC2)ccc1[N+](=O)[O-]] | 2 | 3.1 |
| 2736 | 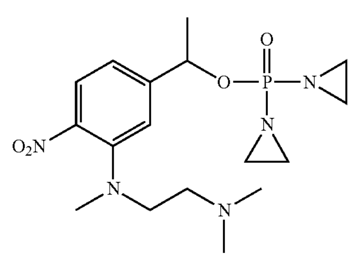 [SMILES: CC(OP(=O)(N1CC1)N1CC1)c1ccc([N+](=O)[O-])c(N(C)CCN(C)C)c1] | 2.8 | 150 |

-continued

| compound | structure | IC$_{50}$ (N$_2$) μM | IC$_{50}$ (air) μM |
|---|---|---|---|
| 2737 | 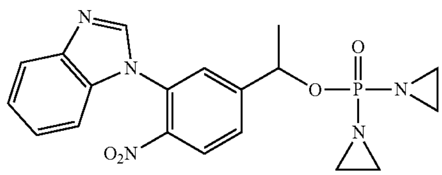 [SMILES: CC(OP(=O)(N1CC1)N1CC1)c1ccc([N+](=O)[O-])c(-n2cnc3ccccc32)c1] | 0.2 | 21 |
| 2738 | 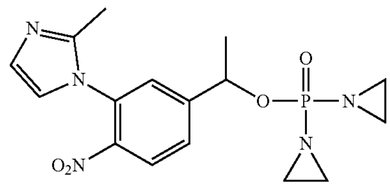 [SMILES: Cc1nccn1-c1cc(C(C)OP(=O)(N2CC2)N2CC2)ccc1[N+](=O)[O-]] | 0.2 | 20 |
| 2740 | 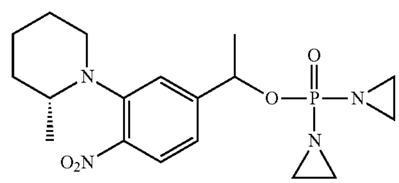 [SMILES: CC(OP(=O)(N1CC1)N1CC1)c1ccc([N+](=O)[O-])c(N2CCCC[C@H]2C)c1] | 1.4 | 24 |
| 2742 | 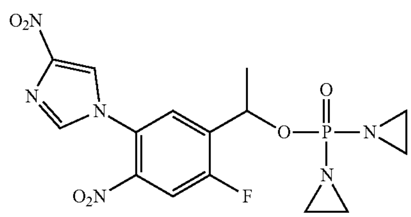 [SMILES: CC(OP(=O)(N1CC1)N1CC1)c1cc(-n2cnc([N+](=O)[O-])c2)c([N+](=O)[O-])cc1F] | 0.1 | 3 |
| 2743 | 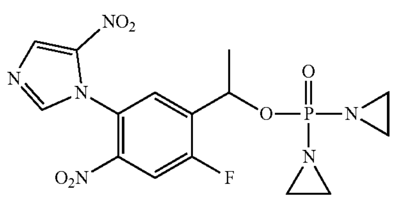 [SMILES: CC(OP(=O)(N1CC1)N1CC1)c1cc(-n2cncc2[N+](=O)[O-])c([N+](=O)[O-])cc1F] | 0.2 | 3.7 |
| 2744 | 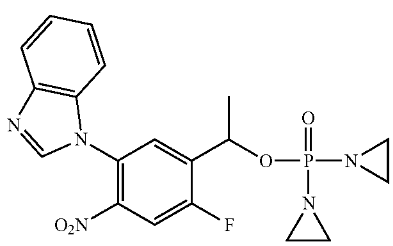 [SMILES: CC(OP(=O)(N1CC1)N1CC1)c1cc(-n2cnc3ccccc32)c([N+](=O)[O-])cc1F] | 0.05 | 2.7 |
| 2745 | 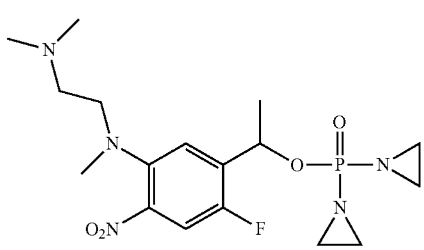 [SMILES: CC(OP(=O)(N1CC1)N1CC1)c1cc(N(C)CCN(C)C)c([N+](=O)[O-])cc1F] | 0.3 | 58 |

-continued
| compound | structure | IC$_{50}$ (N$_2$) μM | IC$_{50}$ (air) μM |
|---|---|---|---|
| 2746 | 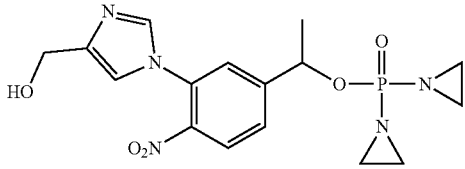 [SMILES: CC(OP(=O)(N1CC1)N1CC1)c1ccc([N+](=O)[O-])c(-n2cnc(CO)c2)c1] | 2.6 | 220 |
| 2747 | 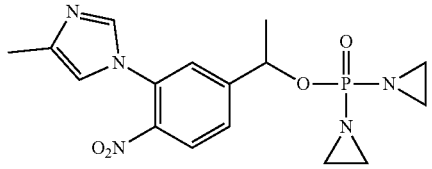 [SMILES: Cc1cn(-c2cc(C(C)OP(=O)(N3CC3)N3CC3)ccc2[N+](=O)[O-])cn1] | 0.3 | 39 |
| 2748 | 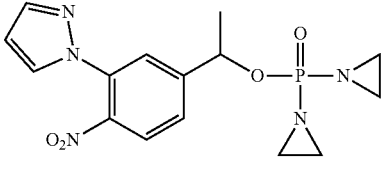 | 0.3 | 38 |
| 2749 | 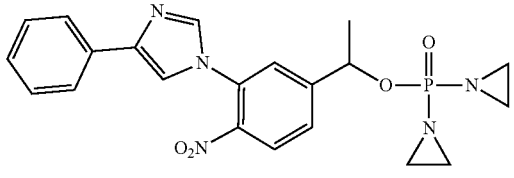 [SMILES: CC(OP(=O)(N1CC1)N1CC1)c1ccc([N+](=O)[O-])c(-n2cnc(-c3ccccc3)c2)c1] | 0.1 | 3 |
| 2750 | 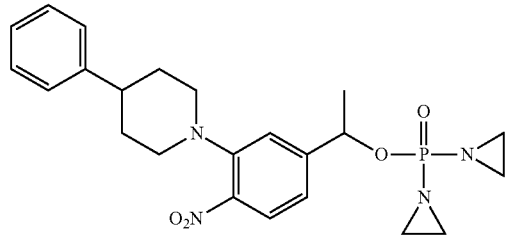 [SMILES: CC(OP(=O)(N1CC1)N1CC1)c1ccc([N+](=O)[O-])c(N2CCC(c3ccccc3)CC2)c1] | 2.4 | 23 |
| 2751 | 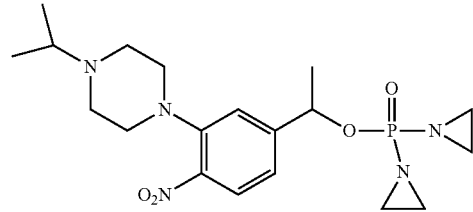 [SMILES: CC(OP(=O)(N1CC1)N1CC1)c1ccc([N+](=O)[O-])c(N2CCN(C(C)C)CC2)c1] | 1.7 | 36 |
| 2752 | 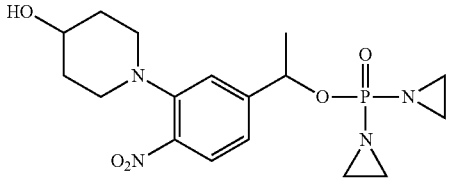 [SMILES: CC(OP(=O)(N1CC1)N1CC1)c1ccc([N+](=O)[O-])c(N2CCC(O)CC2)c1] | 5.7 | 270 |

-continued
| compound | structure | IC$_{50}$ (N$_2$) μM | IC$_{50}$ (air) μM |
|---|---|---|---|
| 2753 | 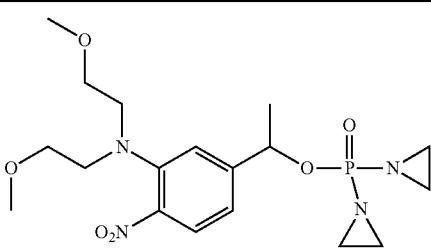 | 3.2 | 19 |
| 2755 | 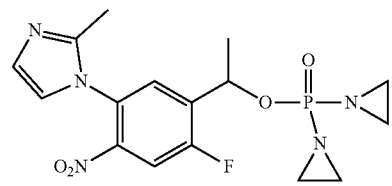 [SMILES: Cc1nccn1-c1cc(C(C)OP(=O)(N2CC2)N2CC2)c(F)cc1[N+](=O)[O-]] | 0.03 | 4.4 |
| 2756 | 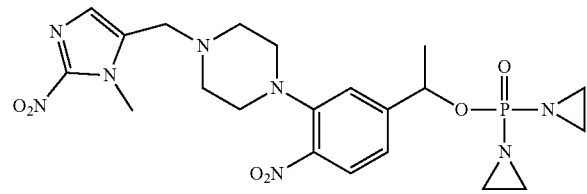 [SMILES: CC(OP(=O)(N1CC1)N1CC1)c1ccc([N+](=O)[O-])c(N2CCN(Cc3cnc([N+](=O)[O-])n3C)CC2)c1] | 2.8 | 45 |
| 2757 | 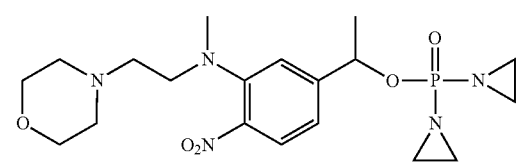 [SMILES: CC(OP(=O)(N1CC1)N1CC1)c1ccc([N+](=O)[O-])c(N(C)CCN2CCOCC2)c1] | 3.8 | 380 |
| 2759 | 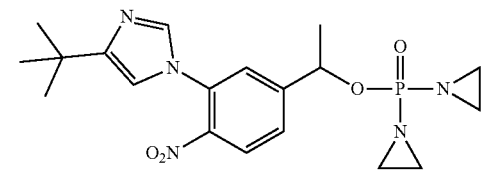 [SMILES: CC(OP(=O)(N1CC1)N1CC1)c1ccc([N+](=O)[O-])c(-n2cnc(C(C)(C)C)c2)c1] | 0.4 | 100 |
| 2760 | 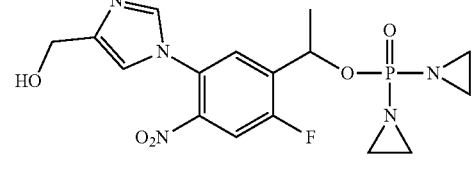 | 2.4 | 53 |
| 2763 | 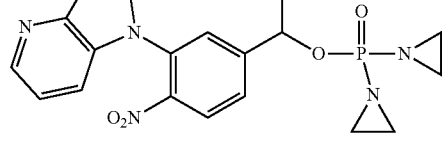 | 0.1 | 5 |
| 2765 | 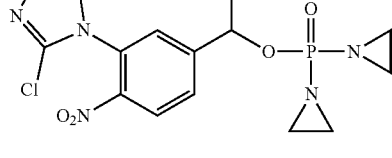 | 0.03 | 8.1 |

-continued

| compound | structure | IC$_{50}$ (N$_2$) μM | IC$_{50}$ (air) μM |
|---|---|---|---|
| 2766 | 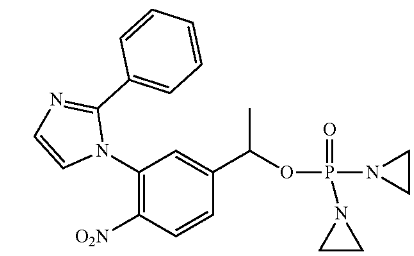 [SMILES: CC(OP(=O)(N1CC1)N1CC1)c1ccc([N+](=O)[O-])c(-n2ccnc2-c2ccccc2)c1] | 0.7 | 4.8 |
| 2767 | 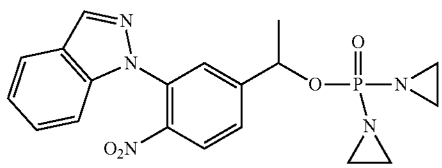 [SMILES: CC(OP(=O)(N1CC1)N1CC1)c1ccc([N+](=O)[O-])c(-n2ncc3ccccc32)c1] | 0.2 | 2.3 |
| 2771 | 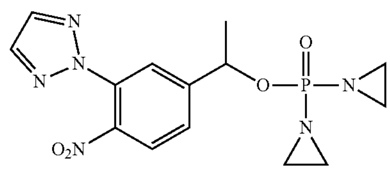 [SMILES: CC(OP(=O)(N1CC1)N1CC1)c1ccc([N+](=O)[O-])c(-n2nccn2)c1] | 0.03 | 14 |
| 2772 | 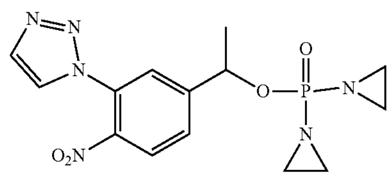 [SMILES: CC(OP(=O)(N1CC1)N1CC1)c1ccc([N+](=O)[O-])c(-n2ccnn2)c1] | 0.05 | 26 |
| 2773 | 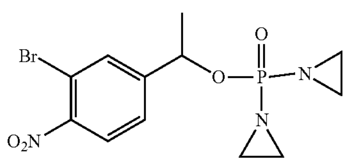 [SMILES: CC(OP(=O)(N1CC1)N1CC1)c1ccc([N+](=O)[O-])c(Br)c1] | 0.7 | 16 |
| 2774 | 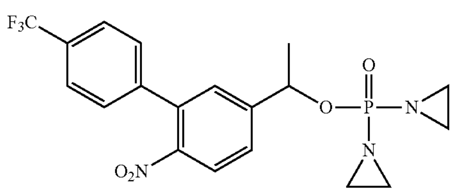 [SMILES: CC(OP(=O)(N1CC1)N1CC1)c1ccc([N+](=O)[O-])c(-c2ccc(C(F)(F)F)cc2)c1] | 0.8 | 3.5 |
| 2775 | 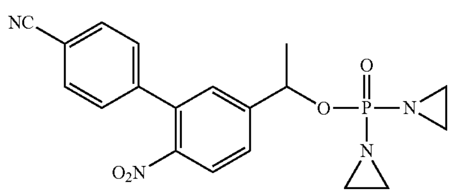 [SMILES: CC(OP(=O)(N1CC1)N1CC1)c1ccc([N+](=O)[O-])c(-c2ccc(C#N)cc2)c1] | 0.3 | 2.5 |
| 2776 | 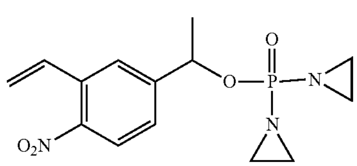 [SMILES: C=Cc1cc(C(C)OP(=O)(N2CC2)N2CC2)ccc1[N+](=O)[O-]] | 0.4 | 2.5 |

| compound | structure | IC$_{50}$ (N$_2$) μM | IC$_{50}$ (air) μM |
| --- | --- | --- | --- |
| 2777 | 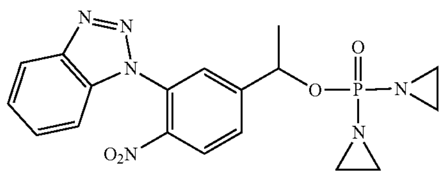 [SMILES: CC(OP(=O)(N1CC1)N1CC1)c1ccc([N+](=O)[O-])c(-n2nnc3ccccc32)c1] | 0.01 | 3.4 |
| 2782 | 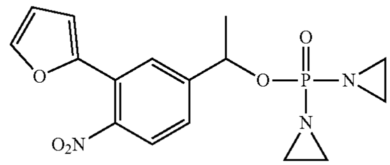 [SMILES: CC(OP(=O)(N1CC1)N1CC1)c1ccc([N+](=O)[O-])c(-c2ccco2)c1] | 1.7 | 41 |
| 2783 | 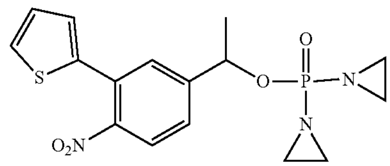 [SMILES: CC(OP(=O)(N1CC1)N1CC1)c1ccc([N+](=O)[O-])c(-c2cccs2)c1] | 1.7 | 51 |
| 2785 | 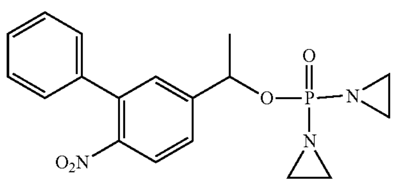 [SMILES: CC(OP(=O)(N1CC1)N1CC1)c1ccc([N+](=O)[O-])c(-c2ccccc2)c1] | 1.6 | 47 |
| 2786 | 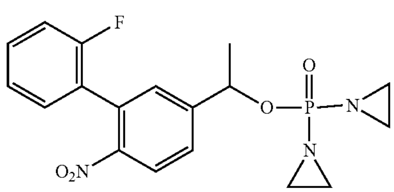 [SMILES: CC(OP(=O)(N1CC1)N1CC1)c1ccc([N+](=O)[O-])c(-c2ccccc2F)c1] | 2.5 | 69 |
| 2787 | 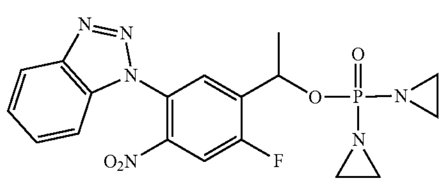 [SMILES: CC(OP(=O)(N1CC1)N1CC1)c1cc(-n2nnc3ccccc32)c([N+](=O)[O-])cc1F] | 0.02 | 2.3 |
| 2788 | 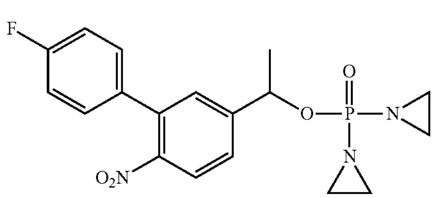 [SMILES: CC(OP(=O)(N1CC1)N1CC1)c1ccc([N+](=O)[O-])c(-c2ccc(F)cc2)c1] | 1.3 | 22 |
| 2789 | 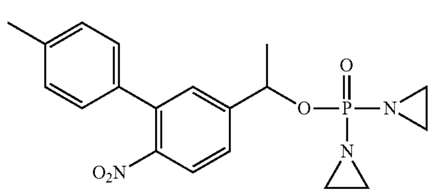 [SMILES: Cc1ccc(-c2cc(C(C)OP(=O)(N3CC3)N3CC3)ccc2[N+](=O)[O-])cc1] | 2.4 | 36 |

-continued

| compound | structure | IC$_{50}$ (N$_2$) μM | IC$_{50}$ (air) μM |
|---|---|---|---|
| 2790 | 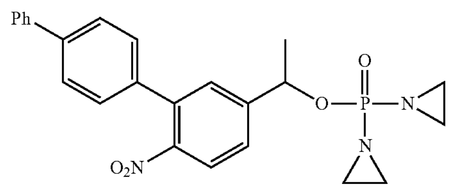 [SMILES: CC(OP(=O)(N1CC1)N1CC1)c1ccc([N+](=O)[O-])c(-c2ccc(-c3ccccc3)cc2)c1] | 1.8 | 4 |
| 2792 | 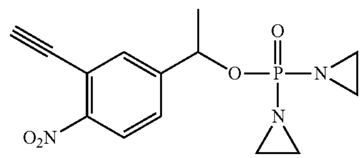 [SMILES: C#Cc1cc(C(C)OP(=O)(N2CC2)N2CC2)ccc1[N+](=O)[O-]] | 0.2 | 3.7 |
| 2793 | 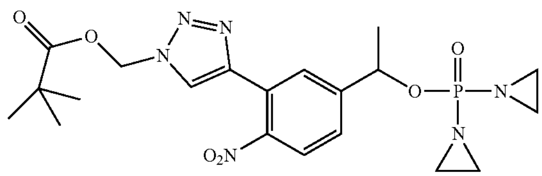 [SMILES: CC(OP(=O)(N1CC1)N1CC1)c1ccc([N+](=O)[O-])c(-c2cn(COC(=O)C(C)(C)C)nn2)c1] | 0.4 | 4 |
| 2798 | 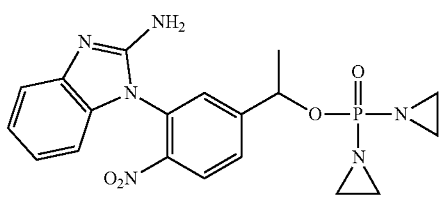 [SMILES: CC(OP(=O)(N1CC1)N1CC1)c1ccc([N+](=O)[O-])c(-n2c(N)nc3ccccc32)c1] | 0.6 | 32 |
| 2799 | 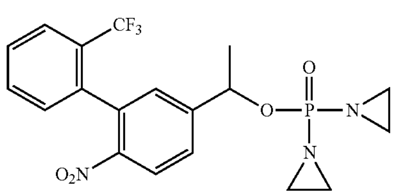 [SMILES: CC(OP(=O)(N1CC1)N1CC1)c1ccc([N+](=O)[O-])c(-c2ccccc2C(F)(F)F)c1] | 2.3 | 37 |
| 2800 | 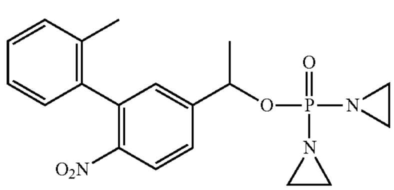 [SMILES: Cc1ccccc1-c1cc(C(C)OP(=O)(N2CC2)N2CC2)ccc1[N+](=O)[O-]] | 1.3 | 30 |
| 2801 | 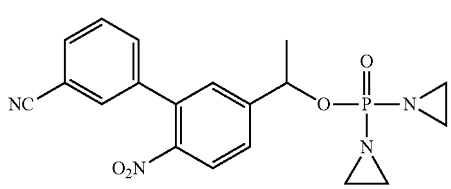 [SMILES: CC(OP(=O)(N1CC1)N1CC1)c1ccc([N+](=O)[O-])c(-c2cccc(C#N)c2)c1] | 2.2 | 47 |
| 2802 | 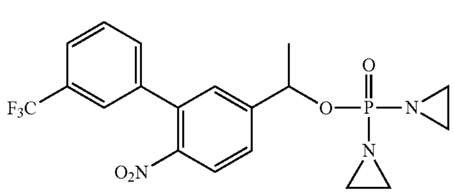 [SMILES: CC(OP(=O)(N1CC1)N1CC1)c1ccc([N+](=O)[O-])c(-c2cccc(C(F)(F)F)c2)c1] | 2.8 | 22 |

-continued

| compound | structure | IC$_{50}$ (N$_2$) μM | IC$_{50}$ (air) μM |
|---|---|---|---|
| 2803 | 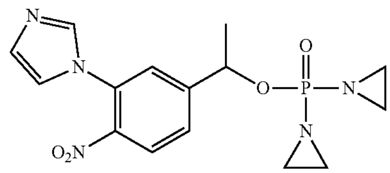 [SMILES: CC(OP(=O)(N1CC1)N1CC1)c1ccc([N+](=O)[O-])c(-n2ccnc2)c1] | 0.3 | 150 |
| 2804 | 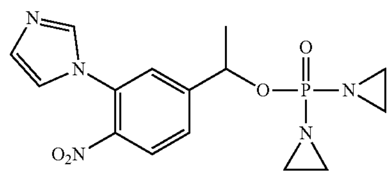 [SMILES: CC(OP(=O)(N1CC1)N1CC1)c1ccc([N+](=O)[O-])c(-n2ccnc2)c1] | 0.6 | 310 |
| 2805 | 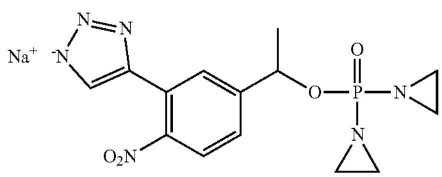 | 1.8 | 320 |
| 2806 | 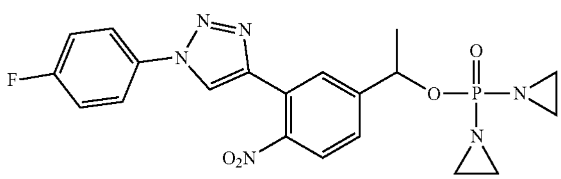 [SMILES: CC(OP(=O)(N1CC1)N1CC1)c1ccc([N+](=O)[O-])c(-c2cn(-c3ccc(F)cc3)nn2)c1] | 0.3 | 5.4 |
| 2807 | 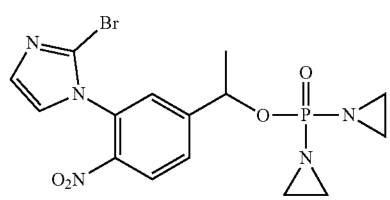 [SMILES: CC(OP(=O)(N1CC1)N1CC1)c1ccc([N+](=O)[O-])c(-n2ccnc2Br)c1] | 0.03 | 13 |
| 2811 | 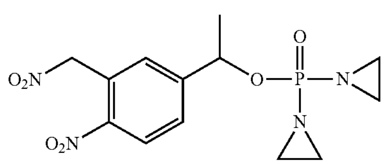 [SMILES: CC(OP(=O)(N1CC1)N1CC1)c1ccc([N+](=O)[O-])c(C[N+](=O)[O-])c1] | 0.1 | 8.4 |
| 2821 | 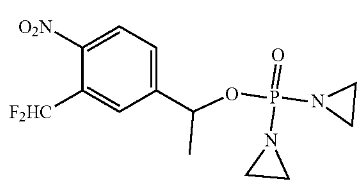 [SMILES: CC(OP(=O)(N1CC1)N1CC1)c1ccc([N+](=O)[O-])c(C(F)F)c1] | 0.05 | 5 |
| 2822 | 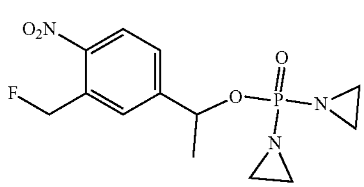 [SMILES: CC(OP(=O)(N1CC1)N1CC1)c1ccc([N+](=O)[O-])c(CF)c1] | 0.3 | 3.1 |

| compound | structure | IC$_{50}$ (N$_2$) μM | IC$_{50}$ (air) μM |
|---|---|---|---|
| 2824 | 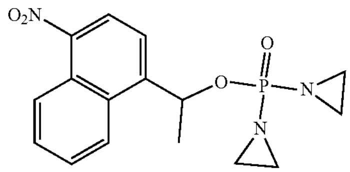 [SMILES: CC(OP(=O)(N1CC1)N1CC1)c1ccc([N+](=O)[O-])c2ccccc12] | 0.02 | 1.7 |

Example 1. Synthesis of TH 2565 and 2566

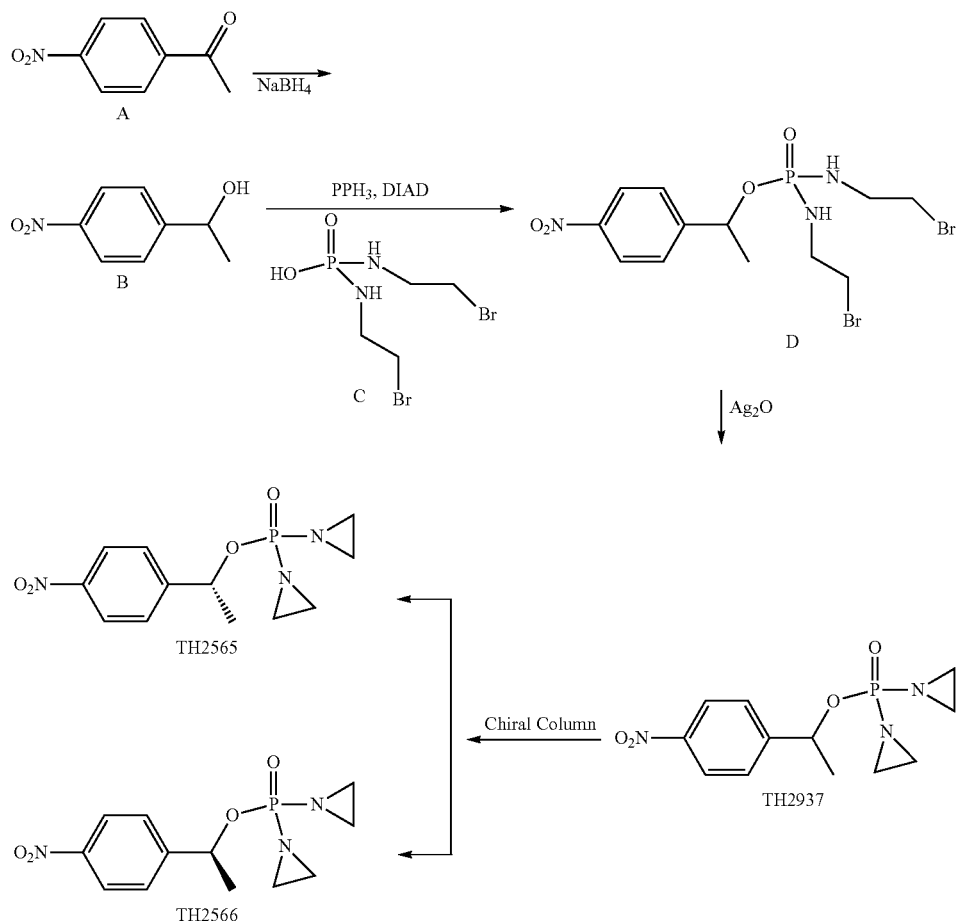

Compound B

NaBH$_4$ (0.38 g) was added to a solution of compound A (1.65 g) in 15 mL of methanol at room temperature. The solution was stirred at for 30 min. The solution was diluted with water (50 mL) and extracted with DCM. The organic layer was dried with Na2SO4. The solvent was removed to get compound B (1.6 g).

Compound D

Under argon, to a suspension of compounds B (1.36 g), compound C (3.7 g), and PPh$_3$ (3.2 g) in THF (40 mL) was added DIAD (2.5 mL) at 0° C. The mixture was stirred from 0° C. to room temperature for 2 hrs. After removal of solvent under vacuum, the residue was separated by flash chromatography on silica gel (Hex:AcOEt=100:70 (v/v)) to yield 1.3 g of compound D.

TH 2937

A mixture of compound D (1.3 g), Ag$_2$O (2.5 g), DIEA (2 mL) in THL (30 mL) was stirred at 50° C. for 5 hrs. After removal of solvent under vacuum, the residue was separated by flash chromatography on silica gel (AcOEt: 20% MeOH/ DCM=70:30 (v/v)) to yield light liquid 0.7 g of TH 2937.

TH 2565 and TH 2566

1.0 g of TH 2937 was separated by chiral column to get 0.48 g of TH 2565 and 0.47 g of TH 2566. 1HNMR(CDCl$_3$)

for TH2565 and TH2566. 1.65 (d, J=6.4 Hz, 3H), 2.02-2.22 (m, 8H), 5.70-5.75 (m, 1H), 7.57 (d, J=8.4 Hz, 2H), 8.23 (d, J=8.4 Hz, 2H).

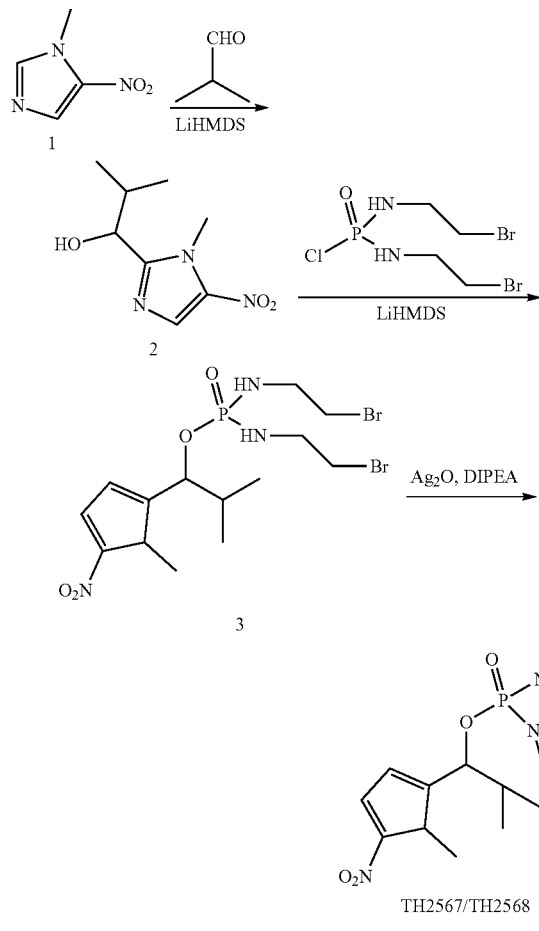

1. Synthesis of Compound 2

To a solution of compound 1 (2.9 g, 22.83 mmol) in THF (35 mL) was added LiHMDS (1.0 M THF solution, 24 mL, 24 mmol) at −40 C under argon. The mixture was stirred at −40 C for 15 minutes.

The aldehyde was added slowly with inner temperature kept below −30 C.

The mixture was stirred at −40 C for 75 minutes before quenched with aqueous saturated NH4Cl solution (10 mL).

The reaction mixture was extracted with EtOAc (40 mL×3), washed with brine (50 mL), dried over Na2SO4.

The solvents were removed under reduced pressure and the residue was purified via flash column to afford clear oil (1.5 g, yield 33%).

1HNMR (CDCl$_3$, 400 MHz) δ: 7.97 (s, 1H), 4.22 (m, 1H), 4.00 (s, 3H), 2.24-2.14 (m, 1H), 1.06 (d, J=6.4 Hz, 3H), 0.93 (dd, J=1.2, 6.4 Hz, 3H)

2. Synthesis of Compound 3

To a mixture of compound 2 (1.5 g, 7.54 mmol) in THF (60 mL) was added LiHMDS (1.0 M THF solution, 8.3 mL, 8.3 mmol) at −78 C under argon.

The mixture was stirred at −78 C for 10 minutes and then a solution of bromine compound (3.7 g, 11.31 mmol) was added slowly.

The mixture was stirred at −78 C and then room temperature overnight.

Solvents were removed under reduced pressure and the residue was purified via flash column to afford a light yellow oil (1.8 g, 49% yield)

1HNMR (CDCl$_3$, 400 MHz) δ: 8.01 (s, 1H), 5.18 (t, J=6.4 Hz, 1H), 4.07 (s, 3H), 3.59-3.02 (m, 8H), 2.41-2.36 (m, 1H), 1.83 (d, J=6.8 Hz, 3H), 0.92 (d, J=6.8 Hz, 3H).

3. Synthesis of TH 2567/2568

A mixture of compound 3 (1.8 g, 3.67 mmol), DIPEA (3 mL), Ag$_2$O (10 g) in THF (45 mL) was stirred at 65 C under argon for 4 hours. Solid was filtered and the filtrate was concentrated to dryness, purified via flash column to afford a clear oil (1.02 g, 81% yield).

1HNMR (CDCl$_3$, 400 MHz) δ: 8.04 (s, 1H), 5.16 (t, J=6.8 Hz, 1H), 4.10 (s, 3H), 2.50-2.41 (m, 1H), 2.24-2.01 (m, 8H), 1.19 (d, J=6.4 Hz, 3H), 0.81 (d, J 6.4 Hz, 3H).

This mixture was separated via chiral HPLC to afford TH 2567 and TH 2568

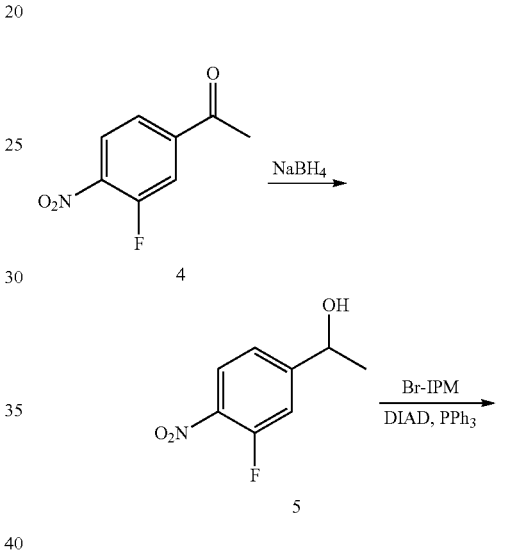

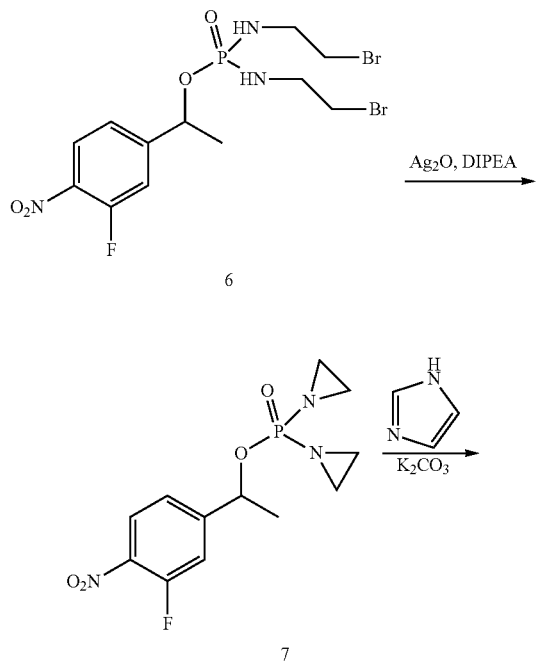

-continued

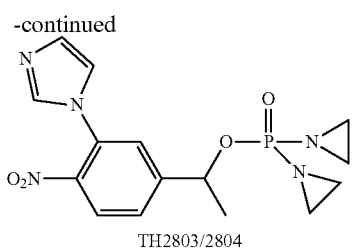

TH2803/2804

1. Synthesis of Compound 5

To a solution of ketone 1 (3.52 g, 19.03 mmol) in MeOH (35 mL) was added $NaBH_4$ (775 mg, 20 mmol) in portions at 0° C.

The mixture was stirred at 0° C. for 1 h, and then the reaction was quenched with acetone (5 mL).

The reaction mixture was concentrated to half of original volume via roto-vapor, the residue was diluted with EtOAc (400 mL), washed with brine (50 mL×3), dried over $Na_2SO_4$.

The solvents were removed under reduced pressure and the residue was purified via flash column to afford a clear oil (3.5 g, yield 99%).

1H NMR ($CDCl_3$, 400 MHz) δ: 8.06 (t, J=8.4 Hz, 1H), 7.35 (d, J=11.6 Hz, 1H), 7.30 (d, J=11.6 Hz, 1H), 5.01-4.99 (m, 1H), 1.52 (d, J=6.4 Hz, 3H).

2. Synthesis of Compound 6

To a mixture of compound 4 (3.5 g, 18.92 mmol) in THF (100 mL) was added Br-IPM (6.99 g, 22.70 mmol), $PPh_3$ (7.44 g, 28.38 mmol) and then DIAD (5.73 g, 28.38 mmol) at 0° C. under argon.

The mixture was stirred at 0° C. for 2 h and then warm to RT over night while stirring.

Solvents were removed under reduced pressure and the residue was purified via flash column to afford a light yellow oil (4.28 g, 47% yield)

1H NMR ($CDCl_3$, 400 MHz) δ: 8.09 (t, J=8.0 Hz, 1H), 8.31 (dd, J=2.4, 13.6 Hz, 2H), 5.52-5.60 (m, 1H), 3.54-3.19 (m, 8H), 1.63 (d, J=6.4 Hz, 3H).

3. Synthesis of Compound 7

A mixture of compound 6 (3.95 g, 8.28 mmol), $Ag_2O$ (12 g) in THF (100 mL) was stirred at 50 C under argon overnight. Solid was filtered and the filtrate was concentrated to dryness, purified via flash column to afford a yellow solid (2.28 g, 87% yield).

1H NMR ($CDCl_3$, 400 MHz) δ: 8.08 (t, J=8.0 Hz, 1H), 7.36 (d, J=11.6 Hz, 1H), 7.31 (d, J=8.4 Hz, 1H), 5.70-5.67 (m, 1H), 2.25-2.08 (m, 8H), 1.64 (d, J=6.4 Hz, 3H).

4. Synthesis of TH 2803/2804

To a mixture of imidazole (62 mg, 0.91 mmol) and compound 7 (260 mg, 0.83 mmol) in DMF (5 mL) was added $K_2CO_3$ (230 mg, 1.66 mmol) at 0° C. The mixture was stirred at room temperature overnight.

Purified via semi-prep HPLC to afford a clear oil.

1H NMR ($CDCl_3$, 400 MHz) δ: 8.02 (d, J=8.4 Hz, 1H), 7.65-7.2 (m, 2H), 7.50 (d, J=1.6 Hz, 1H), 7.24 (s, 1H), 7.08 (s, 1H), 5.81-5.75 (m, 1H), 2.22-2.02 (m, 8H), 1.68 (d, J=6.4 Hz, 3H).

This mixture was separated by chiral HPLC to afford TH 2803 and TH 2804.

Other compounds provided herein are made following this method, upon appropriate substitution of starting materials, which are commercially available or are made according to well-known methods from commercially available starting material. See, e.g., see U.S. Pat. App. Pub. Nos. 2005/0256191, 2007/0032455, and 2009/0136521, and PCT Pub. Nos. 2000/064864, 2004/087075, and 2007/002931, each of which is incorporated herein by reference.

Example 2. In Vitro Human Tumor Cell Line Cytotoxicity Assay

In vitro proliferation data on the H460 non-cell lung cancer human tumor cell line is reported in the table above. $IC_{50}$ values are reported in micromolar and result from exposure of compound at various concentrations for 2 hrs followed by a wash step and addition of fresh media followed by growth and cell viability staining and comparison to a media only treated control.

Specifically, exponentially growing cells are seeded at a density of $4 \times 10^3$ cells per well in a 96 well plate and incubated at 37° C. in 5% $CO_2$, 95% air and 100% relative humidity for 24 hours prior to addition of test compounds. Compounds are solubilized in 100% DMSO at 200 times the desired final test concentration. At the time of drug addition, compounds are further diluted to 4 times the desired final concentration with complete medium. Aliquots of 50 μl of compound at specified concentrations are added to microtiter wells already containing 150 μl of medium, resulting in the final drug concentration reported. After drug addition, the plates are incubated for an additional 2 hours at 37° C., 5% $CO_2$, 95% air, and 100% relative humidity, then the drug is washed off and fresh medium is added and the plates are incubated for addition 70 hrs at 37° C., 5% $CO_2$, 95% air and 100% relative humidity. At the end of this incubation, the viable cells are quantified using the AlamarBlue assay. The drug concentration resulting in growth inhibition of 50% ($IC_{50}$) is calculated using Prism software (Irvine, Calif.), and the results are listed in the table.

The H460 data above demonstrates a substantial antitumor effect with enhanced anti-tumor efficacy observed under nitrogen than under air.

Figure 1B:
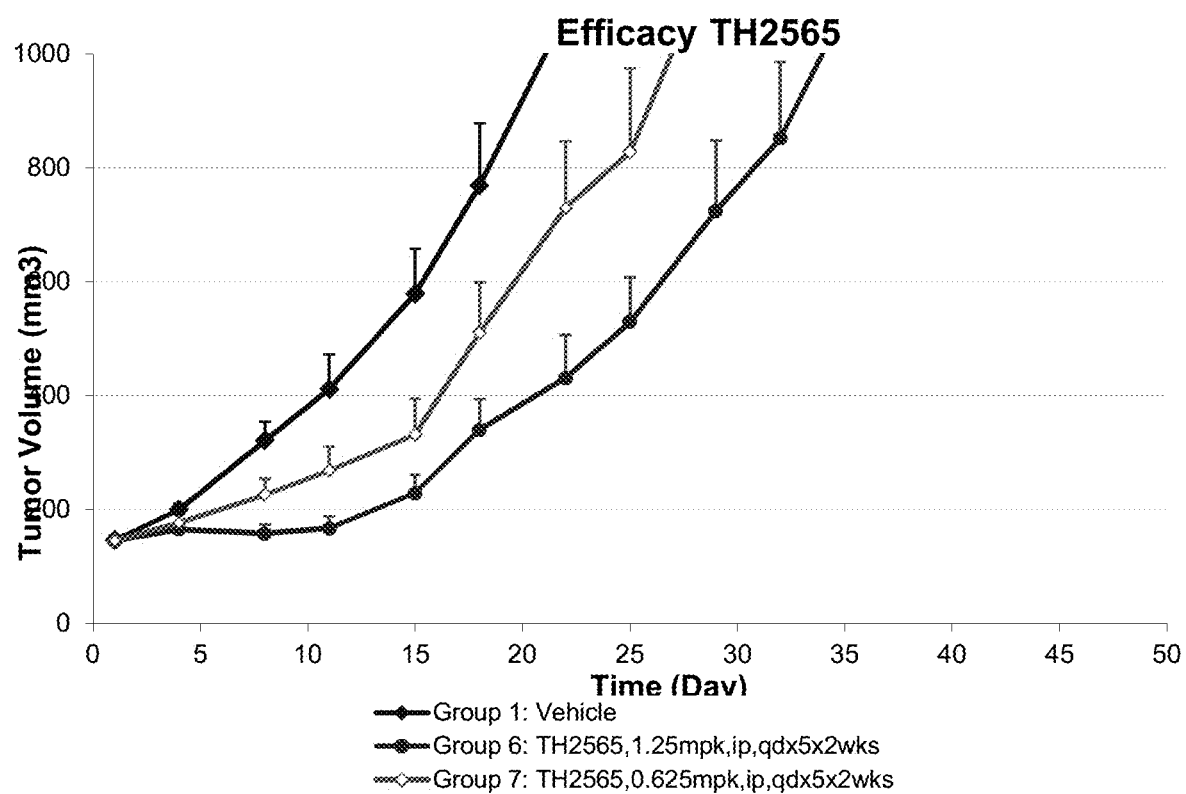
Figure 1C:
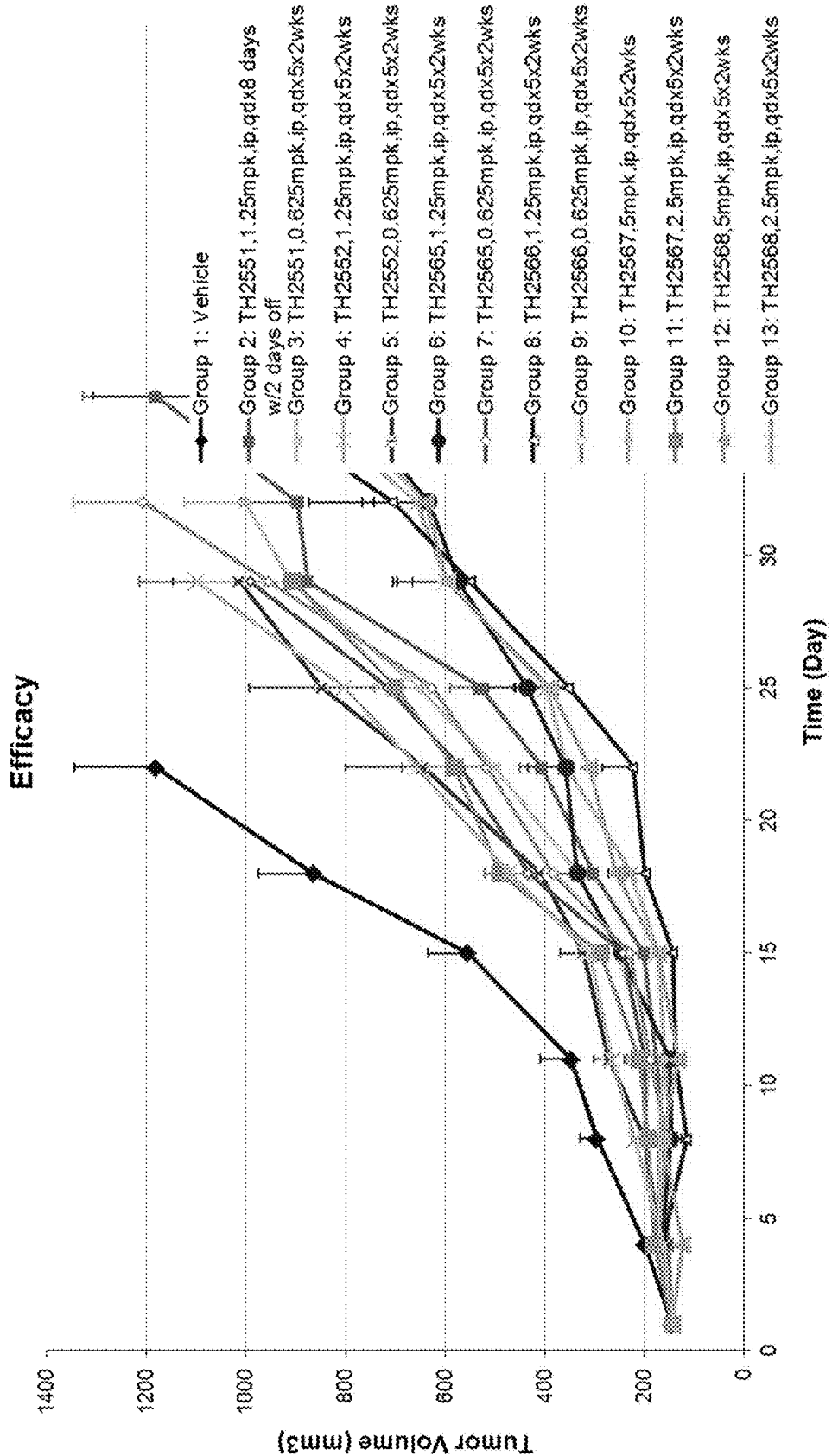

On the basis of the favorable in vitro data for these compounds, their anti-tumor activities in the H460 (NSCLC) human tumor xenograft model were evaluated. H460 cells ($1 \times 10^6$) were subcutaneously implanted in the flanks of pathogen-free homozygous female nude mice (nu/nu, Charles River Laboratories). When tumor size reached 100-150 $mm^3$, animals were randomized to 10 mice per treatment group. All tested compounds were formulated in 5% DMSO, 5% Tween 80 in D5W. The doses of all the compounds were chosen on the basis of preliminary studies to define the MTD of each compound when administered daily for 5 days. On the basis of weight loss and behavioral signs, the MTDs of TH2565 and TH2566 were determined to be 2 mg/kg, respectively. The comparative tumor volume reductions for certain compounds are graphically illustrated in FIGS. 1A-1C.

It should be understood that although the present invention has been specifically disclosed by certain aspects, embodiments, and optional features, modification, improvement and variation of such aspects, embodiments, and optional features can be resorted to by those skilled in the art, and that such modifications, improvements and variations are considered to be within the scope of this disclosure.

The inventions have been described broadly and generically herein. Each of the narrower species and subgeneric groupings falling within the generic disclosure also form part of the invention. In addition, where features or aspects of the invention are described in terms of Markush groups, those skilled in the art will recognize that the invention is also thereby described in terms of any individual member or subgroup of members of the Markush group.

The invention claimed is:

1. A compound selected from:

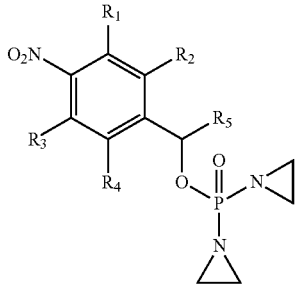

or a pharmaceutically acceptable salt thereof, or a pharmaceutically acceptable solvate of each thereof, wherein
$R^1$ is hydrogen, —$N_3$, CN, $NR^{21}R^{22}$, —$OR^{23}$, —$SO_2(C_1$-$C_6$ alkyl), $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, or ether;
each $R^{21}$ and $R^{22}$ independently is hydrogen, hydroxy, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl, or —$SO_2(C_1$-$C_6$ alkyl); or $R^{21}$ and $R^{22}$ together with the nitrogen atom they are bonded to form a 4-15 membered heterocycle or a 5-15 membered heteroaryl;
$R^{23}$ is hydrogen or $C_1$-$C_6$ alkyl;
$R^2$ is hydrogen or halo;
$R^3$ is hydrogen;
$R^4$ is hydrogen, halo, $C_1$-$C_6$ alkoxy, $C_1$-$C_6$ alkyl, or $C_6$-$C_{10}$ aryl,
$R^5$ is hydrogen, $C_1$-$C_6$ alkyl, $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroaryl; or $R^4$ and $R^5$ together with the intervening carbon atoms between them form a $C_5$-$C_6$ cycloalkyl ring;
wherein the alkyl, alkenyl, alkynyl, cycloalkyl, aryl, heterocycle, heteroaryl, alkoxy and ether groups are optionally substituted.

2. The compound of claim 1 of formula:

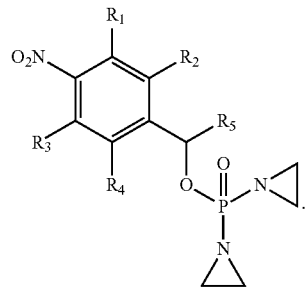

3. The compound of claim 2, wherein $R^1$ is a non-hydrogen substituent, $R^2$ and $R^3$ are hydrogen, and $R^4$ is hydrogen or halo, or $R^4$ and $R^5$ together form a 5 membered cycloalkyl group.

4. The compound of claim 3, wherein $R^4$ is hydrogen.

5. The compound of claim 3, wherein $R^4$ is halo.

6. The compound of claim 3, wherein $R^4$ is fluoro.

7. The compound of claim 3, wherein $R^1$ is $NR^{21}R^{22}$, wherein each $R^{21}$ and $R^{22}$ independently is hydrogen, hydroxy, $C_1$-$C_6$ alkyl $C_2$-$C_6$ alkenyl, $C_2$-$C_6$ alkynyl, $C_3$-$C_8$ cycloalkyl, $C_6$-$C_{10}$ aryl, 4-15 membered heterocycle, 5-15 membered heteroayl, or —$SO_2(C_1$-$C_6$ alkyl); or $R^{21}$ and $R^{22}$ together with the nitrogen atom they are bonded to form a 4-15 membered heterocycle or a 5-15 membered heteroaryl.

8. The compound of claim 3, wherein $R^5$ is a non-hydrogen substituent.

9. The compound of claim 3, wherein $R^1$ is a non-hydrogen substituent; $R^2$ and $R^3$ are hydrogen, and $R^4$ is hydrogen or halo, and $R^5$ is optionally substituted $C_1$-$C_6$ alkyl.

10. A pharmaceutical composition comprising the compound of claim 1 and at least one pharmaceutically acceptable excipient.

11. A method of inhibiting the growth of the tumor comprising administering to a patient in need thereof a therapeutically effective amount of the compound of claim 1.

* * * * *